United States Patent
Anderson et al.

(10) Patent No.: US 10,799,464 B2
(45) Date of Patent: Oct. 13, 2020

(54) DELIVERY SYSTEMS

(71) Applicant: Textile-Based Delivery, Inc., Conover, NC (US)

(72) Inventors: David Anderson, Rockford, MN (US); Jordan Schindler, Tucson, AZ (US); Erik Scott Goebel, Vadnais Heights, MN (US); Nathan Jablonske, Hickory, NC (US); Sandy Wood, East Bend, NC (US); Michael Drzewinski, Long Valley, NJ (US); Justin Jed, Seattle, WA (US)

(73) Assignee: TEXTILE-BASED DELIVERY, INC., Conover, NC (US)

( * ) Notice: Subject to any disclaimer, the term of this patent is extended or adjusted under 35 U.S.C. 154(b) by 0 days.

(21) Appl. No.: 16/216,581

(22) Filed: Dec. 11, 2018

(65) Prior Publication Data

US 2019/0105283 A1    Apr. 11, 2019

Related U.S. Application Data

(63) Continuation-in-part of application No. 15/996,126, filed on Jun. 1, 2018, which is a continuation of application No. 15/583,584, filed on May 1, 2017, now abandoned, which is a continuation of application No. 14/926,949, filed on Oct. 29, 2015, now Pat. No. 9,669,012.

(60) Provisional application No. 62/072,896, filed on Oct. 30, 2014.

(51) Int. Cl.
| | |
|---|---|
| A61K 9/70 | (2006.01) |
| A61K 31/12 | (2006.01) |
| A61K 31/4412 | (2006.01) |
| A61K 31/122 | (2006.01) |
| A61K 31/203 | (2006.01) |
| A61K 31/555 | (2006.01) |
| A61K 31/343 | (2006.01) |
| A61K 9/00 | (2006.01) |
| A61M 37/00 | (2006.01) |
| A61K 47/34 | (2017.01) |
| A61K 31/4166 | (2006.01) |
| A61K 31/616 | (2006.01) |
| A61K 31/573 | (2006.01) |
| A61L 15/44 | (2006.01) |
| A61L 15/40 | (2006.01) |
| A61L 15/24 | (2006.01) |

(52) U.S. Cl.
CPC ............. *A61K 9/70* (2013.01); *A61K 9/0024* (2013.01); *A61K 9/0092* (2013.01); *A61K 31/12* (2013.01); *A61K 31/122* (2013.01); *A61K 31/203* (2013.01); *A61K 31/343* (2013.01); *A61K 31/4166* (2013.01); *A61K 31/4412* (2013.01); *A61K 31/555* (2013.01); *A61K 31/573* (2013.01); *A61K 31/616* (2013.01); *A61K 47/34* (2013.01); *A61L 15/24* (2013.01); *A61L 15/40* (2013.01); *A61L 15/44* (2013.01); *A61M 37/00* (2013.01); *A61L 2300/402* (2013.01); *A61L 2300/41* (2013.01); *A61L 2300/43* (2013.01)

(58) Field of Classification Search
CPC ....... A61K 9/0092; A61K 31/352; A61K 9/70
See application file for complete search history.

(56) References Cited

U.S. PATENT DOCUMENTS

| | | | |
|---|---|---|---|
| 2,799,598 A * | 7/1957 | Philipps | C03C 25/26 139/420 R |
| 3,674,901 A * | 7/1972 | Shepherd | A01N 25/10 424/443 |
| 3,845,791 A | 11/1974 | Zaffaroni | |
| 3,854,480 A | 12/1974 | Zaffaroni | |
| 3,948,254 A | 4/1976 | Zapparoni | |
| 3,992,518 A | 11/1976 | Chien et al. | |
| 3,993,072 A | 11/1976 | Zapparoni | |
| 4,314,557 A | 2/1982 | Chandrasekaran | |
| 4,751,133 A | 6/1988 | Szycher et al. | |
| 5,299,335 A | 4/1994 | Ivester | |
| 5,353,820 A | 10/1994 | Suhonen | |
| 5,531,925 A | 7/1996 | Landh et al. | |
| 5,660,848 A | 8/1997 | Moo-Young | |
| 6,040,251 A | 3/2000 | Caldwell | |

(Continued)

FOREIGN PATENT DOCUMENTS

| | | |
|---|---|---|
| CA | 993358 A1 | 7/1976 |
| CN | 1520297 A | 8/2004 |

(Continued)

OTHER PUBLICATIONS

Japanese Patent Office; Office Action dated Aug. 28, 2019 for Japanese Patent Application No. 2017-522958 and English translation.

(Continued)

*Primary Examiner* — Kyle A Purdy
(74) *Attorney, Agent, or Firm* — Moore & Van Allen PLLC

(57) ABSTRACT

Methods for manufacturing drug delivery systems are provided. The drug delivery systems may include a substrate coated with at least one polymer and at least one active compound. The substrate may include yarns, yarn precursors, threads, filaments, fibers, and/or other suitable substrates. The methods may include disposing a solution including a monomer and an active compound on the substrate. The methods may also include exposing the solution and the substrate to UV light to initiate polymerization of the solution.

20 Claims, 14 Drawing Sheets

(56) References Cited

U.S. PATENT DOCUMENTS

| | | | |
|---|---|---|---|
| 6,103,644 | A | 8/2000 | Sheridan |
| 6,254,883 | B1 | 7/2001 | Jarnstrom et al. |
| 6,596,296 | B1 | 7/2003 | Nelson et al. |
| 6,638,621 | B2 | 10/2003 | Anderson |
| 6,991,809 | B2 | 1/2006 | Anderson |
| 7,033,603 | B2 | 4/2006 | Nelson et al. |
| 7,247,491 | B2 | 7/2007 | Clark et al. |
| 7,316,919 | B2 | 1/2008 | Childs et al. |
| 7,713,440 | B2 | 5/2010 | Anderson |
| 7,736,695 | B2 | 6/2010 | Schwantes et al. |
| 7,780,979 | B2 | 8/2010 | Hu et al. |
| 8,048,446 | B2 | 11/2011 | Lelkes et al. |
| 9,132,204 | B2 * | 9/2015 | McKay .............. A01N 25/34 |
| 9,669,012 | B2 | 6/2017 | Anderson et al. |
| 2002/0102280 | A1 | 8/2002 | Anderson |
| 2002/0119197 | A1 | 8/2002 | Dyar et al. |
| 2004/0009222 | A1 | 1/2004 | Chou et al. |
| 2004/0162580 | A1 | 8/2004 | Hain |
| 2004/0259973 | A1 | 12/2004 | Sakuma et al. |
| 2005/0008776 | A1 | 1/2005 | Chhabra et al. |
| 2005/0048859 | A1 | 3/2005 | Canham et al. |
| 2005/0064176 | A1 | 3/2005 | Terry |
| 2007/0275027 | A1 | 11/2007 | Wen et al. |
| 2008/0020045 | A1 | 1/2008 | Chappa et al. |
| 2008/0057809 | A1 | 3/2008 | Rock |
| 2008/0063687 | A1 | 3/2008 | Chou et al. |
| 2008/0242171 | A1 | 10/2008 | Huang et al. |
| 2008/0248704 | A1 | 10/2008 | Mathis et al. |
| 2009/0158492 | A1 | 6/2009 | Yao |
| 2010/0092529 | A1 | 4/2010 | Chetboun |
| 2011/0142898 | A1 | 6/2011 | Fan |
| 2011/0238036 | A1 | 9/2011 | Ashton |
| 2013/0017243 | A1 * | 1/2013 | Shi .............. A61P 27/02 424/427 |
| 2013/0189342 | A1 | 7/2013 | Patel et al. |
| 2014/0271863 | A1 | 9/2014 | Anderson et al. |
| 2014/0302249 | A1 | 10/2014 | Dhinojwala et al. |
| 2015/0342894 | A1 | 12/2015 | Anderson et al. |
| 2016/0120986 | A1 | 5/2016 | Anderson et al. |
| 2019/0038568 | A1 | 2/2019 | Anderson et al. |

FOREIGN PATENT DOCUMENTS

| | | | |
|---|---|---|---|
| CN | 100572651 A | | 12/2009 |
| CN | 101970560 A | | 2/2011 |
| CN | 103037907 A | | 4/2013 |
| EP | 0395476 A2 | | 10/1990 |
| GB | 1412970 | | 11/1975 |
| ID | 2018/03269 | | 3/2018 |
| JP | 48040924 A | | 6/1973 |
| JP | 60072550 A | | 4/1985 |
| JP | H03-069668 A | | 3/1991 |
| JP | 04234322 A | | 8/1992 |
| JP | 2000096443 A | | 4/2000 |
| JP | 2000212873 A | | 8/2000 |
| JP | 2001097839 A | | 4/2001 |
| JP | 2004536799 A | | 12/2004 |
| JP | 2009518105 A | | 5/2009 |
| JP | 2011511103 A | | 4/2011 |
| JP | 2017515037 | | 6/2017 |
| JP | 2017522365 | | 8/2017 |
| JP | 2018-503598 | | 2/2018 |
| WO | 02087586 A1 | | 11/2002 |
| WO | 2004043435 | | 5/2004 |
| WO | 2007066339 A1 | | 6/2007 |
| WO | 2009067242 | | 5/2009 |
| WO | 2009089346 A2 | | 7/2009 |
| WO | 2010065921 | | 6/2010 |
| WO | 2014143866 | | 9/2014 |
| WO | 2015/184407 | | 12/2015 |

OTHER PUBLICATIONS

European Search Report dated May 11, 2018 for EP Application No. 15854494.0.
International Search Report and Written Opinion dated Jan. 27, 2016 for international application PCT/US2015/058059.
International Search Report and Written Opinion dated Sep. 3, 2015 for international application PCT/US2015/033410.
Anderson, et al., Office Action dated Feb. 25, 2016 for U.S. Appl. No. 14/726,360.
Anderson, et al., Office Action dated Jan. 13, 2017 for U.S. Appl. No. 14/726,360.
Anderson, et al., Office Action dated Sep. 18, 2017 for U.S. Appl. No. 14/726,360.
Anderson, et al., Office Action dated Sep. 2, 2016 for U.S. Appl. No. 14/726,360.
Anderson, et al., Notice of Allowance dated Feb. 2, 2017 for U.S. Appl. No. 14/926,949.
Anderson, et al., Office Action dated Dec. 10, 2015 for U.S. Appl. No. 14/213,808.
Anderson, et al., Office Action dated Jul. 13, 2017 for U.S. Appl. No. 14/213,808.
Anderson, et al., Office Action dated Jul. 7, 2015 for U.S. Appl. No. 14/213,808.
Anderson, et al., Office Action dated Oct. 31, 2016 for U.S. Appl. No. 14/929,949.
Anderson, et al., Office Action dated Sep. 27, 2016 for U.S. Appl. No. 14/213,808.
Champion, et al., Particle shape: A New Design Parameter for Micro- and Nanoscale Drug Delivery Carriers, J control Release, vol. 121, pp. 3-9, Aug. 16, 2007.
Chandrasekaran, et al., Dissolution-Controlled Transport from Dispersed Matrixes, Journal of Pharmaceutical Sciences, vol. 71, No. 12, pp. 1399-1402, Dec. 1982.
Nelson, et al., Application of Microencapsulation in Textiles, International Journal of Pharmaceutics, vol. 242, pp. 55-62, 2002.
O'Neil, et al., Controlling Drug Delivery for the Application of Extended or Sustained-Release Drug Prodcuts for Parenteral Administration, Thesis, Northeastern University, Department of Chemistry and Chemical Biology, pp. 1-73, May 2010.
Shahravan, et al., Encapsulation and Controlled Release from Core-Shell Nanoparticles Fabricated by Plasma Polymerization, J Nanopart Res, Jan. 2012, 14:688, 11 pages.
Weinhart, et al., Switchable, Biocompatible Surfaces Based on Glycerol Copolymers, Chemical Communications, vol. 47, pp. 1553-1555, 2011.
Wongsuwarn, et al., Giant Thermophoresis of Poly(N-isopropylacrylamide) Microgel Particles, Soft Matter, vol. 8, pp. 5857-5863, 2012.
Zu Putlitz, et al.,"The Generation of Armored Latexes" and Hollow Inorganic Shells Made of Clay Sheets by Templating Cationic Miniemulsions and Latexes, Advanced Materials, vol. 13, No. 7, pp. 500-503, 2001.
Chinese Patent Office; Office Action cited in Chinese Patent Application 201580059236.5, Notification of the First Office Action (PCT Application Entry into the National Phase) and English translation; dated Feb. 3, 2020; 10 pages.
Mexican Patent Office; Office Action cited in PCT Patent Application No. MX/a/2017/005399, and English translation, dated Feb. 21, 2020; 11 pages.
Australian Patent Office; Office Action cited in Australian Application No. 2015339203 dated Apr. 16, 2020; 5 pages.
European Patent Office; Office Action dated Jun. 22, 2020 cited in EP Patent Application No. 15854494.0; 8 pages.
Wikipedia, Menthol, 13 pages.
Japanese Patent Office; Japanese Patent Application No. 2017-522958, Office Action, dated Jul. 28, 2020.
Chinese Patent Office; Chinese Patent Application No. 201580059236.5, Office Action, dated Aug. 21, 2020.

* cited by examiner

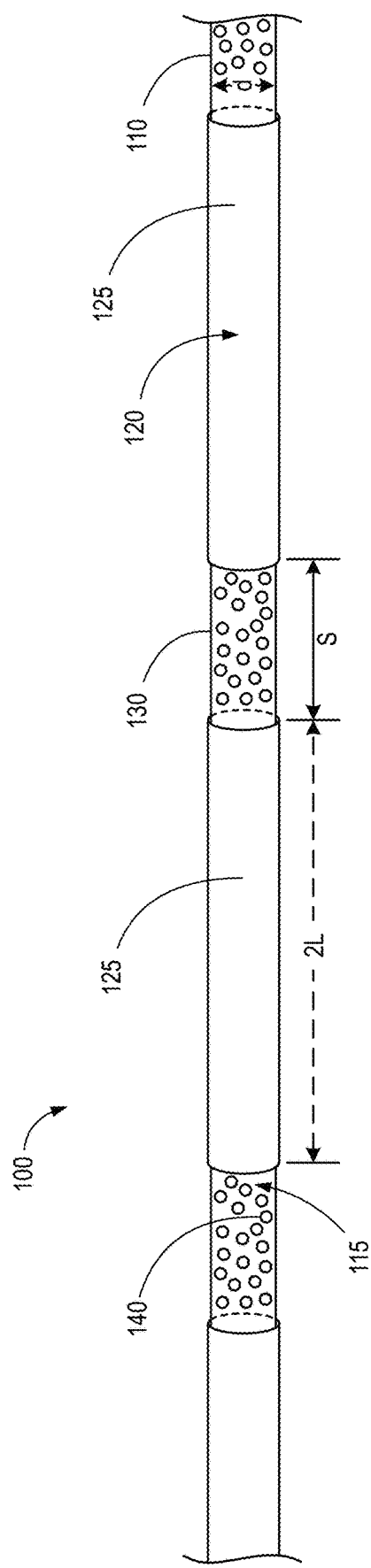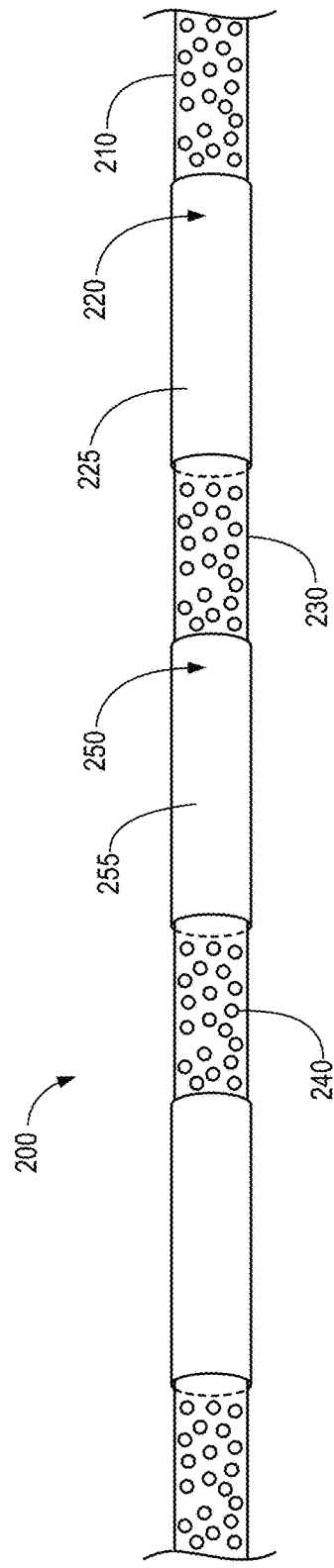
FIG. 1
FIG. 2

DELIVERY SYSTEMS

RELATED APPLICATIONS

This application is a continuation-in-part of U.S. patent application Ser. No. 15/996,126, filed Jun. 1, 2018, titled "Delivery Systems," which is a continuation of U.S. patent application Ser. No. 15/583,584, filed May 1, 2017, titled "Delivery Systems," which is a continuation of U.S. patent application Ser. No. 14/926,949, filed Oct. 29, 2015, which issued as U.S. Pat. No. 9,669,012, titled "Delivery Systems," which claims the benefit of and priority to U.S. Provisional Patent Application No. 62/072,896, filed Oct. 30, 2014, titled "Delivery Systems," all of which are hereby incorporated by reference in their entirety.

TECHNICAL FIELD

The present disclosure relates to materials configured to deliver a variety of active compounds via coated and uncoated yarns and other substrates, as well as methods to produce such yarns or substrates. The materials may be configured to exhibit zero-order or near-zero-order release of the active compounds. The materials may also be configured to protect the active compounds from loss so as to provide a therapeutic amount of active even after repeated uses, wears, applications, and/or launderings. The materials may also be configured to provide substantive protection against hydrolysis and other forms of degradation.

The present disclosure further relates to methods for making and manufacturing drug delivery systems. In certain embodiments, the drug delivery systems may include a substrate coated or covered with at least one polymer and at least one active compound. In particular embodiments, the at least one polymer that coats the substrate may be an acrylate polymer or a methacrylate polymer. In specific embodiments, the at least one polymer may be cross-linked. In further embodiments, the at least one polymer may be a hydrophobic polymer. The substrate may include yarns, yarn precursors, threads, filaments, fibers, and/or other suitable substrates. The methods may include applying or disposing a mixture or solution including at least one monomer and at least one active compound onto the substrate. The methods may also include subject or exposing the mixture or solution on the substrate to UV light to initiate polymerization and/or cross-linking of the solution.

SUMMARY

The present disclosure is directed to yarns and other substrates that are configured to release an active compound at a constant or near-constant rate. The yarns and substrates can comprise a polymer, as well as an active compound. In certain embodiment, the polymer may be a hydrophobic polymer. In particular embodiments, the polymer may be cross-linked. In some embodiments, the active compound can be in crystalline or substantially crystalline form. Other forms of active compounds can also be used, including, but not limited to, amorphous solids and semi-crystalline solids. One or more coatings that are impermeable or substantially impermeable to the active compound may fully or partially occlude the yarn or substrate, thereby providing increased control over the rate and duration of release of the active compound from the yarn or substrate. In certain embodiments, the yarn or substrate is intermittently, selectively, or partially coated along the longitudinal axis or the length of the yarn or substrate. In some embodiments, the ratio of the length of coated segments of the yarn or substrate to non-coated segments of the yarn or substrate is greater than one, and in particular embodiments, substantially greater than one.

Articles of clothing, bedding, bandages, and wound dressings comprising the yarns and/or substrates disclosed herein are also provided.

The present disclosure further provides methods for delivering an active compound to an area of skin of a mammal comprising, for example, contacting the area of the skin of the mammal with a fabric, textile, clothing, or apparel comprising the yarns disclosed herein. In some embodiments, the mammal is a human. In additional embodiments, the active compound is a medication for treating or alleviating the pathological effects or symptoms of a disease or condition.

The present disclosure also provides a method for making or manufacturing the yarns and substrates described herein comprising imbibing a yarn (e.g., a bulked yarn) or substrate with a dispersion or suspension comprising a hydrophobic polymer (e.g., an elastomer), or precursor thereto, and an active compound (e.g., wherein the active compound is in crystalline or substantially crystalline form); polymerizing and/or cross-linking the hydrophobic polymer in the presence of the active compound; and applying a coating to segments or portions of the yarn or substrate such that the yarn or substrate comprises one or more coated segments and one or more non-coated segments, and wherein the coating is impermeable or substantially impermeable to the active compound.

The present disclosure further provides methods for making or manufacturing drug delivery systems. In certain embodiments, the drug delivery systems may include a substrate coated or covered with a polymer and an active compound. In particular embodiments, the polymer that coats the substrate may be an acrylate polymer or a methacrylate polymer. In specific embodiments, the polymer may be cross-linked. The substrate may include yarns, yarn precursors, threads, filaments, fibers, and/or other suitable substrates. The methods may include applying or disposing a mixture or solution including at least one monomer and at least one active compound onto the substrate. The methods may also include subjecting or exposing the mixture or solution and the substrate to UV light to initiate polymerization and/or cross-linking of the mixture or solution.

In certain embodiments, the release of the biologically active compounds from the delivery systems may be at a constant or near constant rate of release. In some embodiments, the drug delivery systems include (i) yarns, yarn precursors, threads, filaments, fibers, and other substrates, (ii) a polymeric coating, and (iii) one or more active compounds. In specific embodiments, the drug delivery systems include (i) yarns, yarn precursors, threads, filaments, fibers, and other substrates, (ii) a acrylate polymer or methacrylate polymer coating, and (iii) one or more active compounds. In other embodiments, the drug delivery systems include (i) yarns, yarn precursors, threads, filaments, fibers, and other substrates, (ii) a cross-linked hydrophobic elastomeric coating, and (iii) one or more active compounds. In particular embodiments, one or more additional coatings that are impermeable or substantially impermeable to the active compound may partially or fully occlude the yarn or substrate to further adjust or control the release rates of the active compound from the cross-linked hydrophobic elastomeric coating. The delivery systems may be used in a variety of applications, including, but not limited to, the making of articles of clothing, textiles, and fabrics. The delivery systems may also be used in methods of treating various conditions and diseases.

In some embodiments, the delivery systems may be configured to exhibit zero-order or near-zero-order release of active compounds to provide benefit through transport of the active compounds from the fabric to the wearer. The delivery systems may be configured to protect the active compounds from loss so as to provide a therapeutic amount of active compounds to a subject even after repeated uses, wears, applications, and/or launderings. The delivery systems may also be configured to provide substantive protection against hydrolysis and other forms of degradation of the active compounds.

The drug delivery systems may include a yarn or another suitable substrate (e.g., yarn precursors, threads, filaments, fibers, etc.), at least one polymer, and at least one active compound. In certain embodiments, the polymer may be hydrophobic and/or cross-linked. In some embodiments, the polymer may be an acrylate polymer or a methacrylate polymer. In particular embodiments, the active compound may be in a crystalline or substantially crystalline form. Other forms of active compounds may also be used, including, but not limited to, amorphous solids, semi-crystalline solids, and/or viscous oils.

In some embodiments, one or more polymeric coatings that are impermeable or substantially impermeable to the active compound may fully or partially occlude the drug delivery systems described herein, thereby providing increased control over the rate and/or duration of release of the active compound from the drug delivery systems. In certain embodiments, yarns, yarn precursors, threads, filaments, fibers, or other substrates treated with, loaded with, coated with, imbibed with, and/or carrying a polymeric matrix or polymer containing at least one active compound may be further wrapped or coiled with additional yarns, fibers or materials to vary the texture, functionality, or aesthetics of the yarns or other substrates and/or the delivery of the active compounds. In addition to clothing or garments, the delivery systems may be used with other fiber- and/or yarn-based materials including, but not limited to, bedding, toweling, bandages, wound dressings, orthopedic devices (e.g., casts), protective athletic equipment (e.g., gloves, pads, and helmets), furniture coverings, leather grips, and/or tight-fitting fabrics (e.g., socks, hats, face-masks, ski masks, scarves, tiaras, chokers, skullcaps, undergarments, skin guards, wrist bands, arm bands, knee pads, bras, nylon stockings, undergarments, athletic supporters, robes, neck bands, head bands, ear muffs, gloves, diapers, poultices, facial masques, paraffin gloves, joint braces, pillowcases, blankets, and sheets).

Additional aspects and advantages will be apparent from the following detailed description, which proceeds with reference to the accompanying drawings.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1 is a perspective view of an embodiment of an intermittently coated yarn comprising a single type of coating.

FIG. 2 is a perspective view of an embodiment of an intermittently coated yarn comprising two types of coatings.

DETAILED DESCRIPTION

Figure 3:
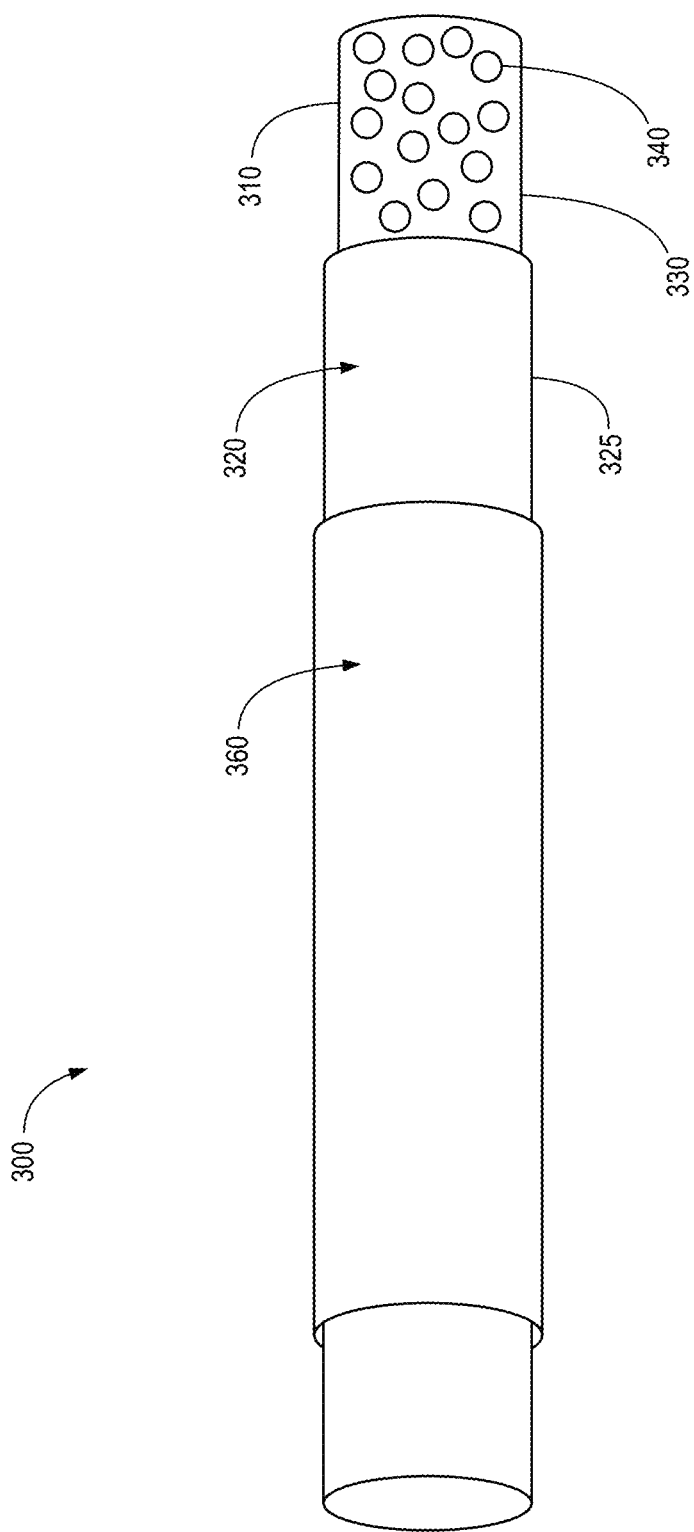
FIG. 3 is a perspective view of an embodiment of a yarn comprising an outer sheath or coating.

The present disclosure provides yarns, yarn precursors, threads, fibers, and other substrates that are loaded with biologically active compounds, compositions, or ingredients (also referred to herein as "actives" and/or "active particles") that are integrated into the yarns, yarn precursors, threads, fibers, and/or substrates. These delivery systems may be utilized to release the active compounds onto or into mammalian tissue, including, for example, human skin.

As used herein, the terms "yarn" and "yarn precursor" include not only finished yarns, but also starting or intermediate fiber-based materials from, e.g., greige cotton or extruded filament, to finished—and as described in certain embodiments, functionalized—yarns (e.g., yarns that are loaded with an active compound), whether on, e.g., a cone or spool or in a textile or fabric. The term "yarn" can also be used to describe individual threads and spun and/or twisted threads. In some embodiments, the yarn may be bulked or textured. Bulked and/or textured yarns can refer to yarns that have been treated mechanically, chemically, or physically (e.g., tension-adjusted) so as to appear to have greater or increased volume relative to the yarn prior to mechanical, chemical, or physical treatment. For example, bulked and/or textured yarns can have a crimped, coiled, or spiral configuration rather than a linear or stretched configuration. Bulked and/or textured yarns can exhibit favorable properties over, e.g., partially-oriented yarn (POY) or other yarns lacking texture and/or bulk.

A number of advantages can accompany the maintenance of bulk or texture in yarns loaded with active compounds as disclosed herein, including comfort, compatibility with established textile production, and high surface area in the non-occluded segments of the yarn. One factor to maintaining texture can be selecting the coating and the matrix polymer such that they rapidly skin-over upon application. In some embodiments, this can be achieved by applying solvent-free (e.g., water-free) matrix polymers and coatings, as aqueous dispersions (often denoted "latex" coatings or paints) may not readily yield a textured or bulked final yarn upon application to a textured or bulked precursor, unless strong conditions are used to flash off the water in very short time (e.g., one second or less).

Embodiments of this disclosure provide yarns, yarn precursors, threads, fibers, fabrics and other textiles, and other substrates that release therapeutically effective amounts of active compounds (e.g., organic active compounds) to the skin of a mammal. Such active compounds can be selected for their dermatological and/or cosmetic benefit, e.g., for skin health and beauty. The active compounds may penetrate into the skin or be delivered to tissue below the skin, including to the boodstream. In certain embodiments, the active compound(s) may penetrate into or through the skin to a depth that depends on the active concentration, the yarn-to-skin (or substrate-to-skin) contact time, physicochemical properties of the active, and/or the structure and condition of the skin.

Embodiments of this disclosure also provide yarns, yarn precursors, threads, fibers, and other substrates that release a therapeutically effective amount of active compound into the bloodstream of a mammal from outside the body. For instance, this may include transdermal delivery, wherein contact of the yarn, yarn precursor, thread, fiber, or substrate with mammalian skin results in transfer of one or more active compounds through the skin and into the bloodstream. Textiles, fabrics, clothing, or apparel comprising yarns, yarn precursors, threads, fibers, and/or other substrates that deliver or release therapeutic amounts of active compounds to, or through, the skin of a mammal that makes contact with the textile, fabric, clothing, or apparel are also provided.

Embodiments of this disclosure also provide fabrics, yarns, yarn precursors, threads, fibers, and other substrates that are able to withstand washing and other stresses (e.g., physical, chemical, thermal, weather) with minimal or no loss of active. Thus, cold washable and hot-washable yarns and yarn precursors that are loaded with active are provided. For example, in a normal washing machine hot wash cycle, these fabrics or yarns may lose less than about 25%, less than about 12%, less than about 7%, less than about 3%, or less than about 1% of the active that was present in the material just before the wash.

The embodiments of the present disclosure can include individual yarns, yarn precursors, threads, fibers, and other substrates, which can provide flexibility through the blending of various active-loaded yarns, yarn precursors, threads, fibers, and other substrates; low shipping costs to overseas mills and markets, especially as compared to finished fabrics (since the medicated yarn need only be a small fraction of the overall fabric yarn). Furthermore, the ability to provide the consumer with medicated thread that can be applied to a fabric with a household sewing machine; and the opportunity to produce a product that is earlier—farther upstream—in the value-added chain that spans from raw fiber to finished textile is also provided.

Furthermore, the various embodiments of the present disclosure can include or utilize cross-linked, hydrophobic polymers (e.g., elastomers such as silicone, rubbers and fluoroelastomers) as protective matrices for actives. Cross-linking (also referred to as "curing," "vulcanizing," and "thermosetting") applied to a dispersion or suspension of active particles in a polymer, oligomer, or monomer matrix—such as a Room Temperature Vulcanizer (RTV), commercial coating or adhesive, chemically reactive linear polymer, etc.—can be employed by the various embodiments of the present disclosure for preparing yarns, textiles, and fabrics that can protect the active against excessive loss during laundering, as well as against a wide range of chemical degradation reactions including hydrolysis, oxidation (depending on the polymer), acid/base-catalyzed reactions, etc. The polymer matrices can be formed from various polymer- or oligomer-based systems, including commercially available elastomeric adhesives, glues, coatings, caulks, sealants, casting materials, and cross-linking systems. The polymers (e.g., elastomers) can also be formed from one or more monomers.

In specific embodiments, the polymers (e.g., elastomers) may be used as a vehicle to load one or more actives into and/or onto the yarn, yarn precursor, thread, fiber, or other substrate and/or immobilize the one or more actives in and/or on the yarn, yarn precursor, thread, fiber, or other substrate. For example, in particular embodiments, one or more actives is combined with a polymer (e.g., elastomer) to form a mixture or solution, which is imbibed by a yarn, yarn precursor, thread, fiber, or substrate. In some embodiments, the final cross-linking (or all of the cross-linking, in some cases including polymerization) occurs in the presence of the dispersed or suspended active particles—resulting in a configuration in which local stresses and strains on the polymer associated with "forcing" solid active particles into an already-cross-linked polymer (e.g., elastomer) are minimized or eliminated. Such strains, at least at high active loadings, can lead to higher permeability and loss of active-protecting effect. Entry of solid active particles (e.g., crystals) into, or formation inside, a previously cross-linked polymeric (e.g., elastomeric) core can also cause distortion of the structure, leaving the active accessible when the purpose of encapsulation is to make it inaccessible. In other embodiments, however, all or a portion of the cross-linking can occur prior to introduction of the active.

In certain embodiments, solid active particles or powders (e.g., crystalline active particles) are used. Solid active particles (e.g., crystalline active particles) may be used, in part, to better achieve dissolution-limited release kinetics. Exemplary forms of active compounds that can be used include, but are not limited to, crystalline or polycrystalline solid particles, semi-crystalline solid particles, amorphous solid particles, plant extracts comprising crystalline or amorphous solid domains of one or more active compounds from the plant, and mixtures or combinations thereof. In further embodiments, the active compounds may include components or fractions of plant essential oils, many of which are crystalline at room temperature and suitable for use. The term "plant essential oils" is as described in U.S. Patent Application Publication No. 2014/0271863, which is incorporated herein by reference in its entirety and which also provides a listing of some of the organic compounds that may be responsible for the desirable or therapeutic effects of these oils.

Various methods for producing particles or powders of active can be used. For example, methods for producing small crystals of an active compound can be categorized according to whether larger starting materials are milled down to smaller size (the "top-down" approach), or microscopic crystals are engineered from the start (the "bottom-up" approach). Methods for milling include high-shear homogenization, high-pressure homogenization (also known as microfluidization), ultrasonication, wet milling, ball milling, and others. "Bottom-up" methods generally rely on precipitation or crystallization in the presence of size-reductive methods such as homogenization and sonication. Active compounds can also be crystallized within microstructures, such as emulsion droplets, liposomes, microparticles, etc., that can limit the size of the resulting crystals.

The active particles (e.g., active crystals) can be dispersed or immobilized in various types of cross-linked, hydrophobic polymer matrices. For example, in some embodiments, the polymer matrix comprises an elastomer in which the active particles are dispersed. Exemplary elastomers include, but are not limited to, silicones, rubbers, halogenated rubbers, polyether block amides, ethylene vinyl acetates, elastolefins, polyurethane elastomers, fluoropolymer elastomers (fluoroelastomers), which can also repel hydrocarbons, thermoplastic elastomers (TPEs), and mixtures and combinations thereof. The polymer matrix can also include an elastomer blended or otherwise mixed with other polymers. In such embodiments, the elastomer domains can be continuous from one end of the elastomer domain to another end such that active particles dispersed within the elastomeric domains can move or diffuse from one end to the other. For example, an illustrative polymer matrix could include both elastomeric domains and crystalline domains, where the elastomeric domains are in continuous communication with one another.

Some of the embodiments disclosed herein include cross-linking so as to lock, hold, or otherwise temporarily retain particles (e.g., crystals) of an active in place and protect them from degradation and premature loss, particularly in the face of stress conditions such as those encountered in laundering.

In certain embodiments, polymers (e.g., elastomers) that have been cross-linked in the presence of dispersed or suspended active are coated along the longitudinal axis or the length of the yarn or substrate. In specific embodiments, polymers (e.g., elastomers) that have been cross-linked in the presence of dispersed or suspended active are intermittently or partially coated along the longitudinal axis or the length of the yarn or substrate. As is more fully described below, mathematical equations given herein prescribe the architecture for yarns, yarn precursors, threads, fibers, and substrates that yield long-duration release with zero-order or near-zero-order release kinetics. For example, one of these mathematical conditions determined by these equations puts a limit on the length of the coated (or more precisely, "occluded") segments of a yarn or substrate, which should not be too long; otherwise, the time needed for an active particle to diffuse to a non-occluded region will be too long to achieve the desired release profile.

The present disclosure provides drug-eluting yarns, yarn precursors, threads, fibers, and substrates that allow for ready integration into or use with existing commercial textile practices and materials. Highly desirable drug-delivery features such as zero order or near-zero-order release kinetics, high loading of active (e.g., drug), stabilization of active, and compatibility with various types of actives are also achieved. The embodiments disclosed herein may be used for improving the health of skin via local delivery of dermatological actives, but are also capable of transdermal delivery of skin-permeable actives and numerous other applications, as described in greater detail below.

In some embodiments, yarns comprising extruded fibers are used. For example, synthetic yarns (e.g., nylon, polyester, etc.) can include extruded fibers. As further detailed below, the active compound and/or the polymer matrix can also be mixed and extruded with the yarn precursor (e.g., nylon or polyester polymers) during formation of the extruded fibers. Further, some embodiments provide active-loaded yarns and substrates wherein the active is in a substantially inert and/or protected state (e.g., crystalline form) and is also protected against degradation by the use of materials that can be processed at room temperature. For example, room-temperature vulcanizing (RTV) polymers and elastomers can be used as materials for the polymer matrix. In such embodiments, wasteful release of active can be limited, at least in part, by 1) the immobilization of active (e.g., crystalline active) within a polymer matrix (e.g., an elastomer matrix) that exhibits negligible or no swelling with water; 2) the coating; and 3) the relatively small proportion of time spent in conditions of wasteful release, such as during laundering of the yarn or substrate.

In particular embodiments, the delivery system disclosed herein comprises a yarn, yarn precursor, thread, fiber, or substrate that includes an active compound that is dispersed or suspended in a polymeric (e.g., elastomeric) matrix, and the yarn, yarn precursor, thread, fiber or substrate containing the active compound and the polymeric matrix is partially or substantially coated or occluded by a coating material that is impermeable or substantially impermeable to the active compound, such that the delivery system provides a dissolution-limited release of the active upon application. In specific embodiments, the percentage of the coated or occluded area, segment, or region that restricts the release of active from the active-loaded polymer (e.g., elastomer) matrix can be between about 80% and about 99.999%, between about 90% and about 99.995%, between about 95% and about 99.99%, between about 95% and about 99%. This particular embodiment of a yarn or substrate that is substantially coated results in release of the active through a relatively small area, thus allowing for extended release of the active over an extended period of time. In some embodiments where a "burst" release is desirable or acceptable, or where rapid release of active is desired even at the expense of constancy of release rate, a coated/occluded percentage of less than 80% may be invoked.

Shown in FIG. 1 is an embodiment of a drug delivery system 100 of the present disclosure. As can be appreciated, although much of the disclosure and Figures may refer to or depict a yarn, other substrates (e.g., yarn precursors, threads, fibers, etc.) can also be used in an analogous manner. The drug delivery system 100 includes the yarn, yarn precursor, thread, fiber, or substrate, which can also be referred to as the core 110 of the drug delivery system 100. A polymer (e.g., elastomer) can be incorporated or loaded into the core 110 to form a polymeric (e.g., elastomeric) matrix 115, which may also be referred to as an inner matrix, inner polymer matrix, or drug matrix. The core 110 can also include active compounds or particles 140 that are dispersed and/or immobilized in the polymer (e.g., elastomer) matrix 115 of the core 110. In certain embodiments, the polymer (e.g., elastomer) and/or the active 140 may be imbibed into the core 110 of drug delivery system 100. Segments of the core 110 may be coated, partially coated, or uncoated. In particular embodiments, the core 110 of the drug delivery system 100 may be partially, selectively, or intermittently coated along the longitudinal axis or length of the core 110. For example, as illustrated in FIG. 1, the core 110 may be intermittently coated with a coating 120 that is impermeable or substantially impermeable to the active 140 in the inner polymer matrix 115. Because the coated or occluded segments 125 of the core 110 are impermeable or substantially impermeable to the active 140 loaded into the drug delivery system 100, they are also referred to herein as "occluded"

segments. The core 110 similarly may comprise exposed, uncoated, non-occluded, or "open" segments 130, which are permeable to the active 140.

As is also shown in FIG. 1, the coated or occluded segments have a length of 2L, while the uncoated or non-occluded segments have a length of S. The diameter of the core is represented by d. In one embodiment, the occluded segments 125 may be configured such that the ratio of 2L/d is larger than about 5, larger than about 10, or larger than about 25. Similarly, the ratio 2L/S of adjacent occluded and non-occluded segments (125, 130, respectively) may be greater than about 1, greater than about 4 (corresponding to 80% occlusion, 20% open), or greater than about 9 (corresponding to 90% occlusion, 10% open). Adjacent occluded and non-occluded segments can refer to segments that are next to each other along the longitudinal axis of the yarn or core 110. In certain embodiments, the drug delivery system 100 may be configured such that the lengths 2L and S of occluded and non-occluded segments (125, 130, respectively) are substantially constant or uniform along the length or longitudinal axis of the yarn or core 110. In other embodiments, the lengths 2L and S of occluded and non-occluded segments (125, 130, respectively) may be varied along the length or longitudinal axis of the yarn or core 110.

Referring to FIG. 2, in certain embodiments of a drug delivery system 200, more than one type of occluded segment 225, 255 may be provided. For example, the core 210 may by coated with a first coating 220 and a second coating 250, each of which may be impermeable, substantially impermeable, or semi-permeable to the active 240. Additional coatings with various functional and physical properties can also be employed (e.g., a third coating, fourth coating, etc.). Coatings 220 and 250 may be configured in any suitable arrangement. For example, they may be adjacent to each other or they may be separated by a non-occluded segment 230, or a combination thereof. In certain embodiments, coatings 220 and 250 may be arranged such that moving axially along the length of the yarn or core 210, one would encounter segments alternating between two or more polymer coatings (e.g., polymer A and polymer B). Uncoated segments 230 may also be included as part of the arrangement. As described more fully below, the pattern and sizing of the coated segments can be selected to control the rate of release of the active 240 from the drug delivery system 200 over time.

In particular embodiments, the coatings 220 and 250 can comprise different materials with different properties. For example, the coatings 220 and 250 can contain polymers having different properties that will affect the rate of release of active 240. For example, in one embodiment, polymer B may be more soluble in water or other aqueous milieu than polymer A, so that the release rate of the active 240 can be relatively low until faster release is "triggered" or commenced by exposure to water (e.g., one or more launderings or rinses, or sweat) that breaks down or degrades the polymer B segments to expose the active-containing core 210. Such degradable materials are known in the art, such as water soluble polymers, poly-lactic acid, poly-L-lactide, poly-glycolic acid and their copolymers, as well as other polyesters, polycaprolactone, biopolymers such as based on collagen or gelatin or other peptide, certain natural gums, certain polysaccharides, chitosan and derivatives, and derivatives and mixtures thereof. Other erodible or biodegradable polymers can also be used.

In other embodiments, two different polymers that are each impermeable to a different type of active compound 240 may be used and arranged in a manner that controls the rate of release of each of the different active compounds 240. Furthermore, in additional embodiments, three or more coatings (e.g., polymers A, B and C) may be used and arranged in a variety of configurations (e.g., alternating) and with or without uncoated segments.

Referring to FIG. 3, a drug delivery system 300 is shown having an outer sheath 360 that covers both the occluded segments 325 (i.e., covered with a coating 320) and open segments 330 of the yarn or core 310. The outer sheath 360 may cover the entire length of the yarn or substrate 310, or one or more selected portions thereof. In some embodiments, the outer sheath 360 comprises a material that breaks down or degrades over time or upon exposure to a "trigger" or particular event (e.g., exposure of a water soluble sheath to water or sweat), thereby leaving the underlying yarn or substrate comprising coated and/or uncoated segments (325, 330, respectively) as described above. In some of such embodiments, the outer sheath 360 may be impermeable or substantially impermeable to the active 340 such that it prevents release of the active 340 until a "trigger" event, at which point the release rate can be controlled by the arrangement of the coated and uncoated segments (325, 330, respectively) underlying the outer sheath 360. The presence of the outer sheath 360 may provide additional adjustments to the desired release of the active 340 over time, including the potential for controlled or delayed release of the active 340 from the drug delivery system 300.

Various materials can be used to prepare the polymeric or inner or protective matrix of the drug delivery system. For example, the matrix may include a polymer or an elastomer that exhibits relatively low toxicity, low allergenic potential, and/or low skin irritation. The matrix also release the active at a rate that delivers an efficacious and reasonably safe dose in the time anticipated or desired for the drug delivery system-tissue contact. In some embodiments, the polymer or elastomer in the polymeric or inner or protective matrix of the drug delivery system may be selected from the following: polysiloxanes (silicones), polyurethanes, polyanhydrides, polyisobutylene, elastin, natural rubber (polyisoprene), chloroprene, neoprene, butyl rubber, styrene-butadiene rubber (SBR), nitrile rubber, epichlorohydrin rubber, fluoroelastomers, polyether block amides, ethylene-vinylacetate (EVA), nylon, polyester, copolymers such as poly(styrene-b-isobutylene-b-styrene), etc. Partial phenyl substitution may be useful in the case of polysiloxanes to improve toughness. In particular embodiments, thermoplastic elastomers, such as styrenic block copolymers (TPE-s, such as Sofprene and Laprene), polyolefin blends (TPE-o), elastomeric alloys (TPE-v or TPV, such as Forprene), thermoplastic polyurethanes (TPU), thermoplastic copolyesters, and thermoplastic polyamides can be used. Illustrative thermoplastic elastomers include Arnitel (made by DSM), Solprene (Dynasol), Engage (Dow Chemical), Hytrel (Du Pont), Dryflex and Mediprene (ELASTO), Kraton (Kraton Polymers), and Pibiflex. Further, in circumstances where faster release rates are desired, a non-volatile and non-toxic solvent (or more generally, liquid) may be used to swell the matrix polymer, if desired. For example, tocopherol can be used.

In some embodiments, the "coating" or "sheath" materials that occlude the active-in-matrix dispersion in the embodiments of this disclosure are of low permeability or impermeable to the active. Many commercial coatings well known to one skilled in the art can be used, with consideration to surface interactions. The coating may be inorganic or organic, or a combination of, for example, inorganic particles or laminates bound together with an organic polymer as binder. The coating may be an inorganic coating, such as a composition of zinc oxide (e.g., 93% zinc oxide), as used in an example provided herein. The coating can also be selected from an organic polymer.

Low permeability can be associated with a highly crystalline polymer, though high crystallinity is not necessarily required if the polymer is in the glassy state near ambient temperatures. In some embodiments, polymers of low crystallinity that nonetheless have high tenacity and low permeability to one or more actives can be used as coatings.

In certain embodiments of making or manufacturing the delivery system disclosed herein, the coating or sheath may be applied by spraying a solution of the coating or sheath in a volatile solvent. Coating materials can be purchased commercially, or can be prepared by dissolving the desired polymer in a suitable solvent. For example, in some embodiments, vinyl polymers, such as polyvinyl chloride (PVC), dissolved in an organic solvent are used as coating materials (as further described in the examples below).

In other embodiments, the coating material includes a high-crystallinity thermoplastic polymer and is processed thermoplastically. In certain embodiments of the present disclosure, the melting temperature of the coating polymer can be low enough to allow processing at temperatures that are low enough to limit thermal degradation of the active. Exemplary polymers for use as coating materials include polypropylene, polyvinyl chloride, PTFE (non-porous), polyvinylidene fluoride (PVDF), PMMA, shellac, polycarbonate (e.g., Lexan), polybutylene terephthalate, epoxy, polyethylene terephthalate (PET), high-density polyethylene, nylon, polyimide, celluloid, acrylonitrile butadiene styrene (ABS), phenol-formaldehyde resin, and polystyrene.

While it is possible for a lower surface energy coating to creep over a higher energy inner matrix so as to occlude the desired non-occluded surface (e.g., the end of a yarn, substrate, or core), this can be prevented. For example, one way to prevent such creeping is to select two polymers with the correct order of surface energies (many elastomers are of low surface energy, e.g., polysiloxanes). Another way is to take advantage of the high modulus of the polymers that one could choose for the sheath or coating polymer, which can exhibit high crystallinity, and arrange the processing conditions such that any tendencies to migrate are limited by the time spent in the molten state.

It may be desired to establish a strong connection of the cross-linked polymer or elastomer to a substrate (e.g., via imbibition). The substrate may in principle be metallic, ceramic, polymeric (glassy, semi-crystalline, or elastomeric), or composite. In some embodiments, the substrate is a yarn, yarn precursor, thread, fiber, or textile. In certain embodiments, the yarn may include a nylon, polyester or acrylic material. An example of a metallic substrate would be finger-worn jewelry, such as a ring, for medicating against arthritis. The polymer or elastomer matrix in such a case could be transparent and thin, so as to preserve the visual beauty of the piece. The substrate can conform to one part of the body, and orthopedic cast and splint materials can be used, as well as wound dressings, and ordinary tight-fitting fabrics such as socks, hats, face/ski masks, scarves, tiaras, chokers, skullcaps, undergarments, skin guards, wrist bands, arm bands, knee pads, bras, nylon stockings, athletic supporters, robes, neck bands, head bands, ear muffs, gloves, diapers, poultices, facial masques, paraffin gloves, joint braces, pillowcases, blankets, sheets, and furniture coverings. Substrates in this disclosure can also be fabrics, both woven and nonwoven, and foams such as polyurethane foams. Exemplary substrates also include fabrics and foams in the form of socks, pillowcases, gloves, and wound dressings. Bamboo fabric can also be used.

In certain embodiments, the yarn or substrate may require greater elasticity or stretch. Thus, the yarn may be plied or twisted with an air-covered yarn (e.g., spandex) to enable additional stretch of the yarn. Additionally, the yarn may be air-covered/air-intermingled (i.e., blowing air onto the yarn and adding a spandex core into the middle of the yarn). These methods are particularly useful for garments that need a lot of stretch such as tights or leggings (or even the elastic portion on the tops of socks).

Embodiments of this disclosure provide yarns, yarn precursors, and substrates that release at a constant or near-constant rate over most of the duration of an extended release profile, the constancy of release being due to the substantially dissolution-limited nature of the release mechanism (described more fully below), and the extended lifetime of release being enabled by the restriction of the non-occluded area over which release can occur from the inner, active-loaded polymer. The percentage of occluded area restricting release of active from the active-loaded inner polymer can be between about 80% and about 99.999%, between about 90% and about 99.995%, between about 95% and about 99.99%, or between about 95% and about 99%. Phrased in terms of non-occluded ("open") regions, the percentage of non-occluded area through which release of active from the active-loaded inner polymer without interference from the coating can be between about 0.001% and about 20%, between about 0.005% and about 10%, between about 0.01% and about 5% or between about 1% and about 5%. Generally, more demanding applications requiring exacting release kinetics will call for a lower open fraction.

As discussed above, the embodiments of this disclosure can be configured to achieve a constant or near-constant rate of release of an active compound from the delivery system. This is of particular value for an active that has a relatively low therapeutic index such that systemic levels should be kept as constant as possible over time, or when the diffusion-limited $t^{1/2}$ profile would waste much of the active during the early-time high release rate.

Certain embodiments of the disclosure rely substantially, or even entirely, on the release characteristics of the polymer matrix that is in direct contact with the active. As described above, the embodiments described herein may include solid active (e.g., crystalline active, active powders, etc.) dispersed in a polymeric matrix, and configured such that the egress of active from the matrix is substantially limited by the appropriate shape and coating of the polymeric matrix, so as to achieve a near-constant rate of active release over an extended period of time.

Referring to FIG. 1, if D is the diffusion rate of the active in the yarn or substrate, K is the dissolution constant of the active in the polymer matrix, R is the effective radius of a constituent fiber of the yarn, A is half the surface area of the open section of length S so that $A=\pi RS$, and the volume of a fundamental repeat unit is $\pi R^2(L+S/2)$, which is approximately $\pi R^2 L$ since $S \ll 2L$. $C_0$ is the initial concentration of active in the polymer matrix (including dissolved and undissolved), and $C_S$ is the saturation concentration of the active in the polymer matrix.

If the open segments of the yarn are (or remain) bulked after imbibition (and coating) (as described below), then, mathematically, this is equivalent to a small value of R indicative of the radius of the substituent fibers, and a higher value of N indicating the (average) number of these same substituent fibers.

The variable N gives the number of constituent fibers of radius R in the cross-section of the yarn, and as would be clear to one skilled in the art, depending on the yarn structure this could be the number of filaments in a multifilament yarn, the number of plies in a twist, the (average) number of independent strands in a bulked yarn, and so forth. The values of N and of the fundamental unit radius R can be defined consistently such that the approximation of the cross-section of the yarn as N circular discs of radius R is a reasonable one. In some instances, the cross-sectional structure in the uncoated, "open" regions can be quite different from that in the coated (occluded) regions. The subscript "1" will correspond to the open regions and "2" to the occluded regions in this disclosure.

With this nomenclature, and as to embodiments wherein S<<L, the following approximate equation for the release rate (flux) of active per unit length (here, per centimeter) of yarn holds to within a constant numeric and dimensionless factor:

$$Q=C_s(DK)^{1/2}R_1SN_1/L$$

This equation gives the release rate at steady-state when in the dissolution-limited case, exact conditions for which are given herein. The release rate equation is most easily interpreted when the entire "open" area on the yarn is abutting a receiving surface such as skin or mucosal tissue. Because only a portion of a given yarn will be touching or contacting skin, the equation represents a maximal release rate that is to be multiplied by the fractional open area that is touching or contacting skin or another receiving medium.

Since the volume-weighted average concentration is $C_0$ (which includes both dissolved and undissolved active), and again assuming S<<L, we have the approximate expression for M, the total mass of active released over the entire release profile:

$$M=C_0R_2^2N_2$$

The duration of release T is then:

$$T=M/Q=(L/S)\cdot(N_2/N_1)\cdot(R_2^2/R_1)\cdot(C_0/C_s)/(DK)^{1/2}$$

which, in the case where the fibrillar structure is approximately the same in the coated regions as in the open regions, simplifies to:

$$T=M/Q=(L/S)\cdot R\cdot(C_0/C_S)/(DK)^{1/2}$$

In most cases, even if the open and occluded regions have very different fibrillar structures, the total cross-sectional area will nevertheless be the same in the open and occluded regions, even if the fibrils in the occluded regions are "glued" together by the coating so that N is reduced (often to 1). In these cases, the following equation can be used, derived by setting the total cross-sectional areas over all fibrils equal in coated and open regions:

$$N_1\cdot R_1^2=N_2\cdot R_2^2$$

And using this relationship we can write:

$$T=(L/S)\cdot R_1\cdot(C_0/C_S)/(DK)^{1/2}$$

This equation, which holds quite broadly (unless the open regions are engineered to be a different total cross-sectional area of the core matrix) tells us that the internal/fibrillar structure inside the coated regions—which may be fibrillated and bulked even after coating—does not substantially affect the duration of release. This is a result of the fact that diffusion in the long ($L>>R_2$), coated segments is very closely approximated as a one-dimensional process whether there is bulk ($N_2>1$) or not ($N_2=1$).

From these equations, it can be seen that the duration of release T can depend on more than one structural dimension. In particular, it can depend on the term $(L/S)\cdot R_1$.

As an example of kinetic control, the degree of bulking after imbibition can be adjusted by adjusting the tension on the yarn during imbibition and curing. Open regions of the final yarn will maintain this bulk if handled properly, because they need not be exposed to the coating. This tension-adjusted bulking can greatly reduce $R_1$ and therefore the term $(L/S)\cdot R_1$. This could strongly affect the duration of release T. In general terms, the small thicknesses, in 2 dimensions, of yarn, and particularly of fibrils, means that surface-to-volume ratios will be higher than in volumetric or even thin-film configurations. For a given volume of active-loaded matrix, a higher surface area of open regions means that release rates (Q) are relatively higher and duration of release (T) lower. In order to achieve longer durations, the most efficient way is generally to reduce surface areas by decreasing the open length S. In some cases, in order to obtain desired release characteristics it might be necessary to reduce S to only a few hundred microns.

Since the release rate does not depend on L whereas the duration does, the duration of release can be controlled by adjusting the length of the occluded segments without affecting the rate of release; this is because at steady-state, the active concentration is at the saturated value $C_s$ regardless of L (recognizing that this steady state lasts longer as L increases). In short, the present disclosure provides not only for near-constant drug release, but also for independent control of release rate Q and duration of release T. This can be an important advantage of the present disclosure because in practice, the choice of the polymer that forms the inner matrix will be driven by many factors other than D and K, such as cost, ductility, processing ability, cross-linking considerations, tack/adhesion, etc. Thus, one does not want to be restricted in polymer selection in order to meet kinetics requirements (D and K) without an easily adjustable parameter such as the aspect ratio of the yarn or substrate.

Diffusional distances, represented by the occluded segment length L in the present disclosure, can be much longer than those represented by the film thickness in other types of structures. Thus for the same chemistry, i.e., the same values of D and K, the duration of action can be very long—an inherent advantage of the embodiments described herein—as compared to a traditional nonwoven patch. However, increasing S can counteract this effect.

It is emphasized that in this disclosure, $C_0$ is the volume-averaged concentration of active within the cross-linked polymer or elastomer including both the dissolved and undissolved active. The ratio $C_0/C_S$ can be at least about 5, or greater than or equal to about 10. The matrix can be heavily "supersaturated" in view of the large amount of crystalline material, relative to the active that is dissolved in the matrix at the time of first use (the latter of which can lead to an exaggerated burst effect if the ratio $C_0/C_S$ is not large enough).

In the practice of the embodiments of this disclosure, particularly in embodiments where the final yarn is bulked in the open segments, the very small value of $R_1$, measured literally in 10 s of microns in many cases, will mean that S may need to be small in order to reach a targeted duration T; the desired length S might be as low as 100 microns. In such cases, the best processing method for adding the coating might be to physically clasp or adhere ring-shaped masking solids; simply applying a screen that does not contact the yarn may not be sufficient to control the spread (or variability thereof) of coating to within the required precision.

As is stated above, embodiments of this disclosure may provide yarns, yarn precursors, and substrates that release at a near-constant rate per area of skin contact over a dominant portion of the duration of an extended release profile, the constancy of release arising from the dissolution-limited nature of the release mechanism, which in turn results from conformance to the following mathematical conditions, where D is the diffusion rate and K the dissolution constant of the active in the core, and u=1 centimeter is a standard unit of length:

1. The ratio $D/(K \cdot u)$ is greater than about 10, greater than about 30, or greater than about 100;
2. The ratio $KLR_1/(SD)=(LR_1/S) \cdot (K/D)$ is less than about 0.1, less than about 0.025, or less than about 0.01; and
3. The ratio $2L/S$ is between about 4 and about 30,000, between about 9 and about 10,000, or between about 99 and about 3,000.

Dimensionality may be manipulated in a very surprising way in the present disclosure, as can be demonstrated with reference to the three conditions noted above. The following compares 2-D and 1-D cases of when an intermittent or patterned coating is used to provide predominantly linear release through the "occlusion-dominance" approach discussed in the previous paragraphs. In a patch of material in which the matrix for the active is not woven, e.g., a gel, liquid, or nonwoven polymer film, then within the "mostly occluded" approach disclosed herein, the diffusion of the active will quite generally be primarily in two dimensions ("2-D"), namely in the plane of the thin film. The patterns of occluded/non-occluded regions can fall into two classes:

2-D pattern: a pattern that is repeating in two dimensions and conforms to one plane group listed along with the 230 space groups in the International Tables of Crystallography.

1-D pattern: there is only a one-dimensional "line group." The only such pattern in the present context consists of alternating occluded and non-occluded segments, each of fixed width.

In some embodiments, the 2-D pattern can be inherently inferior. For example, the 2-D pattern case can be simplified to a fundamental "cell," best viewed as, e.g., a hexagon, wherein a particular hexagon is made up of all points that are closer to a particular node than to any other node. In the present context, each node represents the center of a non-occluded (or "open") region. By analyzing a single representative hexagon, the result is easily extended to the entire plane. Key to the issue of dimensionality is that the proportion, f, of non-occluded area varies as the square of the radius, measured outward from the nodal center of the open region:

$$f=(3/\pi)(R_O/R_H)^2$$

where $R_O$ is the radius of the open region and $R_H$ is the radius of the circle that circumscribes the hexagon. Functionally, $R_H$ is a measure of the diffusional length, over which concentration gradients drive movement of active particles, e.g., from crystals in occluded regions to release at open regions. From the point of view of maintaining zero-order release kinetics predominantly over the release profile, the ratio $R_O/R_H$ can be less than about 0.2, or less than or equal to about 0.1; but, from an area-coverage perspective, the a real fraction $(R_O/R_H)^2$ can be much higher than the about 0.01 to about 0.04 that corresponds to $R_O/R_H$ values of about 0.1 and about 0.2, respectively.

Thus, according to this approximate analysis, if one were to use a 2-D pattern in which each diffusional path to a node was, for example, 90% occluded—as is desirable for maintaining a high linearity in the release profile—then the "open"/non-occluded fraction would be under 1%. A value this low would be generally unacceptable for delivery to the skin; even if having only 1% of the area active is consistent with a desired (high-potency) drug, the end-user will experience "spotty" delivery over the desired area of coverage. In some cases this may be acceptable, but in general the sensitive nature of skin would not allow for spotty coverage to this extent. One can anticipate that a significant fraction of people would develop some sort of discoloration if relatively large amounts of drug were focused on a few small dots of contact.

Instead, utilizing the simple "1-D pattern" approach, namely, alternating occluded and non-occluded stripes (or strips, rows, etc.), then the ratio 2L/S provides both the real fraction of open regions and the open fraction of the diffusional/gradient length; one does not square the ratio as in the 2-D case. Thus, a "striped" pattern allows adjustment of the coating pattern to achieve a quasi-zero-order kinetic profile without having to sacrifice the fraction of open area for release. Furthermore, the stripes may be arranged perpendicular to the main longitudinal axis of the yarn or at any angle thereto, or a combination of both.

Two general approaches to making or manufacturing the delivery systems are disclosed herein, embodiments in which an intermittent coating are used are referred to herein as the "imbibition/coated method" (or I/C), and extrusion-based methods. To some extent this mirrors the division between natural fiber-based methods, exemplified by cotton processing, and synthetic filament methods exemplified by polyester.

The core-sheath configurations described herein can be produced by processes that are best described with reference to existing methods known in the art, such as dyeing, (co-)extrusion, etc. A solid or powdered form of the active (which may be obtained by wet or dry milling, controlled precipitation, spray-drying, etc.) of the desired size distribution (e.g., crystal size distribution) is first mixed into the matrix polymer (e.g., elastomer), with elevated temperature if required to soften the polymer. In some embodiments, the matrix polymer is either un-cross-linked at this point, or only lightly cross-linked; further cross-linking, if desired, can be applied at any stage subsequent to this mixing, and may be engineered to occur during the mixing in a single operation (e.g., due to the elevation in temperature). Standard processes of intensive mixing, kneading, or alternatively convective mixing or homogenizing (e.g., at elevated temperatures), and the like can be applied. Melt-blowing with an impacting stream of the powder may also be used, thus creating fiber contemporaneously with powder/polymer mixing. Notwithstanding this, we now describe the step of loading active particles (e.g., crystals) into and/or onto a pre-existing yarn.

Imbibition is the act of contacting an existing substrate, which has the geometric configuration of a filament, fiber, thread, yarn, or woven textile, and is capable of taking up the matrix polymer (RTV, adhesive, etc.) or a precursor thereof (e.g., a pre- or partially cured matrix polymer) to a significant or threshold imbibition loading, for example, between about 5% and about 1,000% of the substrate weight, between about 10% and about 200% of the substrate weight, or between about 20% and about 100% of the substrate weight. The substrate may be, for example, yarn, yarn precursor, thread, fiber, or some other elongated substrate.

When multifilament yarn, and particularly yarns of plant or animal source or bulked yarns, are passed through reservoirs containing polymers (e.g., elastomers), RTV, or other (hydrophobic) matrix polymer precursor fluid, they spontaneously absorb or imbibe this fluid. Furthermore, the active particles (e.g., active crystals) dispersed in this fluid are also quite generally imbibed by the substrate yarn.

As substrates, many natural fibers have cuticles that are known in the art to be capable of taking up amphiphilic and hydrophobic materials. For example, cotton is capable of imbibing very high loadings of silicone, for example, frequently more than twice the weight of the original fiber.

Within the Imbibition/Coating (I/C) production approach, there is a continuum of processing schemes that may be best delineated by the following well-defined reference points:
  "Yarn-level imbibition": Individual yarns are imbibed in this approach.
  "Warp imbibition": In a weaving process, the yarns or fibers making up the "warp" are imbibed.
  "Weft imbibition": In a weaving process, the yarns or fibers making up the "weft" are imbibed.
  "Textile-level imbibition": A two-dimensional textile or fabric is imbibed.

Advantages of performing processing on individual yarns as compared to on textiles have been discussed above.

Advantages of textile-level imbibition are well-known to one skilled in the art. Entire two-dimensional textiles and fabrics can be imbibed in one unit operation. There are very strong reasons for doing the imbibition step at the textile level.

However, in the present disclosure, a coating step must follow, and if the imbibition step is performed at the textile level, then so must the coating step. In some embodiments, the coating is applied intermittently along the length of each yarn and, in particular, has "open" areas that are millimeter or sub-millimeter in length. In particular embodiments, saturation imbibition (soaking a textile in an imbibing RTV or other elastomer) is followed by a process that yields a precisely controlled intermittent coating. A woven textile is geometrically complex enough that ordinary saturation coating at the textile level may not be discriminating enough to yield the desired intermittent coatings of the present embodiments, satisfying the desired range of open fraction. Nevertheless, by introducing small masking pieces (clasps, masking tape, coating-immiscible fluid, etc.) at intervals on either the warp or the weft of a woven textile, an intermittent coating may be achieved by saturation dip-coating of a "prepared" woven in a coating liquid, after which the masking pieces may be removed.

Some embodiments of the present disclosure are produced by first drawing a bulked yarn, such as cotton or multifilament polyester, through a paste created by dispersing the active in the matrix polymer/elastomer, which can be an RTV silicone that is close to 100% silicone, and of viscosity less than about 10,000 centipoise, or less than about 1,000 centipoise.

In particular embodiments, imbibing a bulked or texturized yarn, such as a polyester or nylon yarn, can be performed at relatively high speeds (e.g., on the order of about 10 meters per second), so as to achieve a desired loading of polymer matrix. For example, in some embodiments, a bulked or texturized yarn can be drawn through a 1 centimeter length of Novagard 200-260 at about 10 meters per second to yield an increase in Denier or weight of the yarn by approximately 75%. In such embodiments, the yarn will spend approximately one millisecond of time in the Novagard, and yet pick up an additional 75% weight from the imbibed RTV.

After imbibing the paste, the yarn may be cross-linked, or "cured," by exposure to humidity, elevated temperature, or irradiation. After curing, an intermittent coating can be applied, with a very low uncoated fraction (<1%), and open areas of yarn-direction length (S) below 1 millimeter. Methods for curing the matrix polymers provided in this disclosure are exemplified by the Novagard® RTV silicones. Novagard 200-260 cures by an oxime reaction upon contact with humidity in the air. Cross-linking time can be reduced by increasing the humidity of the air coming into contact with this RTV; as with most any reaction, reaction time can also be reduced by raising the temperature, but it is already assumed in this discussion that, as one skilled in the art would know, temperature during curing is generally raised to a value that is elevated but with due caution paid to temperature stability of excipients and, most of all, the active.

Other commercially available polymer or monomer preparations including some from Novagard cure by irradiation, most conveniently by ultraviolet light. Some of the Novagards cure in as little as two seconds under sufficiently intense UV light.

The curing time—or skin-over time—can be less than 1 hour, less than 5 minutes, or less than 20 seconds. It is particularly helpful in the practice of the embodiments of this disclosure, in part because in many cases the imbibed yarn prior to completion of curing is strongly adhesive, becoming more tenacious with the extent of curing. In certain embodiments of the present disclosure, the imbibed but not-yet-cured yarn should only minimally contact any other solid material, including other yarn whether imbibed, cured, or otherwise. Not-yet-cured means that the extent of curing is sufficiently low that the viscoelasticity at outer surfaces, "skinning", is not well developed enough to keep the still-tacky material from strongly adhering to other solid surfaces as does a glue in the early curing.

The imbibition step, as well the curing step, may be performed with a mast accumulator. For example, in one embodiment, yarn runs off a creel, through the imbibing chamber and onto an accumulator. One can use large mast accumulators 6 to 10 feet or more in length, such as a Belmont AC50, thus providing the means to generate a 3- to 5-minute dwell time of the treated yarn with few contact points. This enables the just-imbibed yarn to cure for 5 or more minutes without touching itself or having prolonged contact with the equipment and sticking to itself. The yarn is moved via rope or rubber coated belts (Teflon coated); the yarn only has around 10% contact with these mechanized belts. The flyer arm at the input of the mast accumulator can be controlled to place the yarn at controllable intervals along the rope. Utilizing multiple flyer arms at 180- or 120-degree intervals should enable the input of multiple ends of yarn running onto one mast accumulator. A cone winder or multiple cone winders pull from the end of the mast accumulator winding the yarn onto a cone (or multiple cones). These accumulators are widely available and ideal for commercial scale production. They are able to run at 600 yards per minute, with controls that enable variable speed as needed. The yarn runs onto and off the accumulator at the same speed if desired. A trial run on the equipment was able to handle 100 Denier yarn. A small Iro weft accumulator, or yarn path, may also be used to generate some additional cure time or, once the yarn has come off the accumulator, the accumulator can be used to facilitate the next intermittent (spray coating) step. A yarn path may be configured using metallic or Teflon coated bars, spread vertically or horizontally across a facility to run the yarn around and through.

Coatings and sheaths of the embodiments of this disclosure can be applied to imbibed yarn via one of two general processes. Coating fluid can be applied continuously or intermittently to a yarn, or the yarn can be intermittently "masked," with small masking pieces (clasps or tape, etc.) that are applied to the yarn prior to coating and removed afterward.

Further, metering devices can be used to control the rate of "imbibing" onto the yarn. The wicking devices have easy screws to control the tension on the yarn, thereby allowing for greater control over how much matrix is imbibed into the yarn. Wicking/oiling devices, ceramic guides and finish applicators also may be used to apply the drug/matrix to the yarn.

For example, an intermittent coating may be achieved by attaching relatively small or tiny clamps to the yarn, for example, at regular intervals before the yarn undergoes coating. Another method for blocking or "masking" the yarn from coating over specific stretches of yarn—ultimately the "open" regions of the final yarn—is to coat these regions with a polymer or powder that either substantially repels the subsequently applied coating, or substantially removes the coating when it is removed, e.g., the removal being effected by dissolution into water or solvent, air impingement, or in some cases, simple bending or twisting.

Dissolution-limited release polymeric yarns and textiles of the present embodiments may, as discussed herein, be partially coated or "sheathed" with one or more active-impermeable polymers, called "A" (or "B," "C", etc.), "coating," or the "occluding polymer" herein. In some embodiments, it can be advantageous to arrange for reactive groups in or at the surface of an imbibed yarn, particularly in such a way that the subsequently applied coating bonds covalently to the underlying imbibed yarn, thus preventing disassociation of portions of the coating from the final yarn. Generally speaking, reactive groups that can form covalent bonds with one or more components of the coating are incorporated at the surface of the imbibed yarn, in one of three general approaches. In one approach the matrix material which is imbibed in or on the yarn comprises these reactive groups; these may be the same reactive groups already present in the imbibed polymer used for cross-linking the polymer, and the coating is applied before the cross-linking has gone to 100% completion; or they may be present on another material in the mixture that is imbibed, such as another polymer which preferably cross-links together with the main imbibed polymer. In a second approach, an interlayer material is applied after the imbibing step, wherein the interlayer material (which need not necessarily be a polymer) covalently bonds to both the imbibed matrix and the coating; in the case of a silicone matrix, particularly useful interlayer materials are provided, for example, by ISurTec, Inc., under the product family name "Photoprime," and can be conveniently activated by UV light. A third approach uses irradiation of the imbibed yarn to create reactive groups at the surface. For example, glow discharge, corona discharge, gas atmosphere plasma, flame plasma, atmospheric plasma, low pressure plasma, vacuum plasma, glow-discharge plasma, and plasma etching can be used to introduce reactive groups at the surface. Other methods include exposure of the substrate material to strongly acidic or basic solutions, or to solutions of reactants such as peroxides, or compounds that react with carbonyl groups that are ubiquitous in polymers such as diazomethane, Grignard and Wittig reagents, primary and secondary amines, dilithio oximes, sodium alkynides, and hydrides, etc. In the case where the substrate is a polysaccharide such as a cellulose, reactants that react with such polymers are well known to one skilled in the art, such as boron-based reactants, etc. Alternatively, the substrate material can be formulated so as to contain the desired reactive groups. Exemplary reactive groups can include, but are not limited to, isocyanates, alcohols (hydroxyls), oximes, silanols, epoxides, amino and carboxylate acids groups, etc.

The production of alternating coatings containing two or more polymers may be achieved by varying the methods and processes described above. For example, a roll-coater could be used wherein the roll-coater has interspersed sectors feeding the two polymers. Alternatively, two spray guns loaded with different polymers can be alternately sprayed or masked. Another possibility is an emulsion or liquid suspension that is sprayed through a single nozzle, resulting in immiscible and thus phase-separated depositions of a first polymer (from the emulsion droplets) interspersed with a second polymer from the continuous phase of the emulsion or suspension. This has the potential to make segments of the first polymer that are very short (e.g., less than 100 microns in length), but larger than the fibril diameter of typical texturized clothing yarns.

As previously discussed, in some embodiments, extrusion-based methods can be used in manufacturing the yarns disclosed herein. For example, extrusion-based methods can comprise extruding a mixture comprising the active compound, polymer (e.g., elastomer) matrix materials, and yarn precursor (e.g., polymers) to form fibers, fibrils, or filaments that are incorporated into a yarn. In particular embodiments, the polymer/active dispersion, which may at elevated temperatures in fact be a solid-in-liquid dispersion or even an emulsion if the melting point of the active is low, can be extruded into the desired shape, typically a filament, and the coating or "sheath" applied either concomitantly using co-extrusion, or to the extruded fiber using standard methods of coating, such as spray coating, spray-drying, electrospray, fluidized bed coating, vapor deposition, etc. Roll-coating processes might be advantageous if the fibers are produced as a (woven or nonwoven) web, which after coating would be subsequently broken or cut into segments of the desired length.

Following the extrusion of a monofilament, continuous fiber, it gives a good "feel" to the yarn if this monofilament is processed (e.g., like polyester), e.g., the monofilament can be processed by cutting and collecting into a "staple," bulked fiber.

The delivery systems disclosed herein may be used in a variety of applications. The applications discussed below are representative and illustrative, though certainly not all-inclusive. Suitable actives for use in the various applications are also provided below.

In certain embodiments, the textile comprising the yarn may comprise both the medicated yarn of this disclosure along with ordinary, non-medicated yarn. For example, in woven textiles, the warp can be traditional yarn and the weft yarn of the present embodiments. In other embodiments, only medicated yarn may be used.

According to the present disclosure, large dosages of several grams or more per dosing, that are difficult to deliver as pills or in other dosing forms, can be administered through skin-contacting material (e.g., clothing) in a way that is convenient, private, and even fashionable. Also, forgetful patients, such as schizophrenics, children, the elderly, Alzheimer's or pre-Alzheimer's sufferers, and the like can be assured of taking their medication (i.e., increased compliance) by virtue of simply lying on a pillow at night, or putting on their socks or another article of clothing such that they are in contact with the medicated material. The knitting of such materials may be facilitated by treating the yarns of the present disclosure with a lubricant (e.g., 2% to 3% lubricant) prior to knitting.

Importantly, long-term use of a transdermal approach can be used without engendering the risks or downsides of occlusive and/or adherent patches or bandages. Certain areas of the body may be well-suited to delivery of an active substance via clothing, but not well-suited to more traditional methods of delivery. For example, the feet or hands may be particularly well-suited to delivery via socks or gloves, whereas other topical delivery methods known in the art may not provide as efficient delivery because of the risk of being rubbed off, etc. Further, current fabric-based products of purported medicinal value, such as diabetic socks for example, which have not been provided with the obvious medicaments due to washing requirements, can now be medicated and yet still remain fully washable.

Specific classes of compounds that can be incorporated as actives and delivered include demulcents, emollients, lubricants, vasoconstrictors, antibiotics and antiseptics, antihistamines, immunosuppressants, local anesthetics, antiallergics, antifungals, vasoprotectants, anticoagulants, mucolytic and proteolytic compounds, antiglaucoma drugs, and anti-inflammatories, anesthetics, anti-helminthic, analgesics, steroids, non-steroidal inhibitors of the inflammatory cascade, anti-neoplastic, anti-angiogenic, calcineurin inhibitors, anti-ocular hypertensives, antivirals, antibacterials, neuroprotectants, anti-apoptotics, medications for dry eye, pupil dilating medications (mydriatics and cycloplegics), ocular decongestants, antioxidants, photosensitizers, photodynamic therapy agents, mast cell stabilizers, monoclonal antibodies, quinolone antibiotics, and intra-ocular pressure lowering agents. Specific ophthalmic pharmaceutical actives in addition to the above which may be incorporated in the embodiments of the present disclosure are: acetazolamide, amikaci, anecortave, antazoline, apraclonidine, atropine sulfate, azelastine, azithromycin, bacitracin, bacitracin zinc, betaxolol hydrochloride, bimatoprost, brimonidine, brinzolamide, bupivicaine, carpbachol, carteolol hydrochloride, ceftazidime, ciprofloxacin hydrochloride, clindamycin, cromlyn, cyclopentolate hydrochloride, denufosol, dexamethasone, dexamethasone sodium phosphate, diclofenec sodium, dipivefrin hydrochloride, diquafosol, dorzolamide, doxycycine, edetate sodium, emadastine, epinastine hydrochloride, epinephrine, erythromycin, fluocinolone, 5 fuoruracil, fluoromethalone, fluoromethalone acetate, flurbiprofen sodium, fomivirsen, ganciclovir, gatifloxacin, gentimicin, gramicidin, imopenemn, ketotifin, ketrolac tromethamine, latanoprost, lerdelimumab, levocabastine, levofloxacin, levubunolol hydrochloride, lidocaine, lodoxamide, lotoprednol etabonate, medrysone, methazolamide, metipranolol, mitomycin, moxifloxacin, naphazoline, nedocromil, neomycin, ofloxacin, olopatadine, oxacillin, oxymetazoline hydrochloride, pegaptanib, pemirolast, pheniramine, phenylephrine hydrochloride, photofrin PIR 335, pilocarpine hydrochloride, polymixin B, prednisolone acetate, prednisolone sodium phosphate, proparacaine, ranibizumab, rimexolone, scopolamine hydrobromide, sulfacetamide sodium, tetracaine, tetrahydrozoline hydrochloride, timolol, timolol maeate, tobramycin sulfate, travoprost, triamcinolone acetonide, trimethoprim, tropicamide, unoprostone, urea, vancomycin, and verteporfin. Also suitable are derivatives, analogs, and prodrugs, and mixtures and combinations thereof.

In certain embodiments, actives that are dyed or colored may be utilized. Colored actives provide several potential advantages, such as providing the user visual confirmation of activity, favorably modifying skin color or tone, and aiding in manufacturing QA/QC. Colored actives that may be incorporated into yarns of the embodiments include, but are not limited to, Curcumin, Methylene Blue, Gentian Violet, Dantrolene sodium, and Oil Red O. These actives cover a range of therapeutic effects including anticancer, antibacterial, antifungal, antispasmotic, antioxidant and anti-inflammatory effects.

An overview of various classes of conditions and treatments that may utilize the various embodiments of the present disclosure are described below.

For application of actives to portions of skin suffering from abnormalities or for cosmetic improvement, the present embodiments offer direct skin contact, localizable coverage, washing machine compatibility ("washability"), rapid rate of release, continuous coverage through the night if desired or, as a patch, throughout the day or night. Actives for particular skin conditions may include tea tree oil for acne, eczema, psoriasis, etc. In addition to acne, other skin conditions for which the embodiments described here are particularly useful include rashes, skin allergies, folliculitis, impetigo, erysipelas, cellulitis and dermatitis.

In applications that can be considered therapeutic, cosmeceutic, cosmetic, etc., embodiments of the present disclosure can improve skin condition and appearance via the release of, for example, vasodilators, rubefacients, ceramide, emollients, dermoprotective, lipolytic, or epithelializing compounds.

The embodiments described herein can be of particular utility in medication- or antimicrobial-releasing socks, because socks must be washed so frequently, and the need is inherently high due to the relatively high rate of foot- and sock-related disorders, risks, and inconveniences, such as offending odors and the associated risks of infections (not only bacterial but also fungal and viral), and more serious risks faced by the growing incidence of diabetes.

In addition to acne, eczema and psoriasis, the following conditions are treatable, or preventable, with embodiments of the present disclosure: scleroderma (which often leads to Raynaud's syndrome), neutrophilic dermatosis, urticaria, xeroderma-pigmentosum, Goltz syndrome, recessive dystrophic epidermolysis bullosa, Harlequin ichthyosis, hypertrichosis, Morgellons disease, dermatofibrosarcoma protuberans, and infections such as human papilloma virus (HPV). Scleroderma may occur in both non-systemic and systemic forms, and while the delivery systems of the present disclosure can be suited for treating the non-systemic form (e.g., with a fabric that would release an active oil extract from *Salvia miltiorrhiza* (Danshen) and/or from *Capparis spinosa*), they are effective against the systemic form as well. *Salvia miltiorrhiza* and *Capparis spinosa* work against scleroderma in two distinct mechanisms, so that delivery of a combination of the two oils via the delivery systems of the present disclosure may be particularly efficacious.

In addition, delivery systems of the present disclosure can provide for wound dressings that are non-adherent, non-occlusive for oxygen transport, and non-irritating. Wounds for which the systems can be used include chronic wounds, such as malignancies, persistent infections (e.g., gangrene), decubitis and diabetic ulcers, and other ulcers of traumatic, venous, or ischemic origin. While the delivery system can be used as a primary dressing, it can also be effective as a secondary dressing, delivering medicament through the primary dressing.

In one embodiment related to wound dressing, a delivery system of the present disclosure may be used as an insert or lining to a cast, splint, sling or brace. There are over 6.8 million broken bones just in the U.S. every year, many requiring the use of a cast, splint, sling or brace for treatment. In the case of individuals treated for scoliosis, for example, patients must wear a full body cast and lie in bed for 3 to 6 months. There are many common negative issues associated with wearing casts for prolonged periods of time, including but not limited to, allergic reactions, skin sores, infections, joint stiffness, muscle loss, offensive odor, burns and compartment syndrome, which greatly limits blood flow. Many or all of these negative side effects could be effectively treated or mitigated by delivery of appropriate actives via the systems of the present disclosure. Such an application could employ the disclosed systems in the form of an insert or lining to a cast, splint, sling or brace. The cast/insert system could be designed such that the insert could be removed, daily if necessary, for washing without interfering with the supportive and protective functions of the cast or brace. The insert could provide release of antimicrobials, growth factors, analgesics, and skin toning/cosmeceutical actives, and release medicaments or essential oils designed to increase blood circulation. Several classes of actives are beneficial for treatment of wounds and may be used with the systems of the present disclosure, including but not limited to growth factors, clotting factors, local anesthetics, steroids, vitamins, minerals, antimicrobials, or in milder wounds antiseptics and bacteriostats.

Delivery systems of the present disclosure can deliver sleep-/relaxation-aiding actives both into the bloodstream through release into the skin, and into the brain through the trigeminal neural pathway via nasal inhalation. Many compounds and oils from nature that induce relaxation often have analgesic action as well. Thus, due to action by these substances at one or more opioid receptors, embodiments of the disclosure can be applied to release these actives and—potentially with combined transdermal and trigemical (inhalation) delivery routes—achieve a synergistic combination of anxiolytic and analgesic actions. One embodiment that can include a combination of two actives is the combination of lavender and Melissa essential oils. Plant essential oils that are purported analgesics include lavender, wintergreen, Roman chamomile, marjoram, peppermint, rosemary, thyme, vetiver, helichrysum, ginger, lemongrass, copaiba (copal), and balsam fir. Specific fractions or components of these oils, such as menthol, can be used as well, particularly if they have substantial volatility. In some embodiments, the vapor pressure of the active at 35° C., for inhalation/trigeminal neural pathway delivery, is equal to or greater than about 0.01 Torr, greater than about 0.1 Torr, or greater than about 0.5 Torr. A drug with lower vapor pressure than this may still be practical if the potency of the drug is very high, such as with carfentanil.

Extracts and purified compounds from the following plants have been reported in the literature to have central-acting analgesic activity, and these could be incorporated into the various embodiments of the present disclosure for relief of pain and, in many cases, for relaxation as well: *Abutilon indicum, Acacia ferruginea, Acacia nilotica, Achillea ageratum, Acicarpha tribuloides, Aconitum carmichaelii, Aconitum flavum, Aconitum japonicum, Acorus calamus, Adansonia digitata, Afrormosia laxiflora, Agastache sinense, Ageratum conyzoides, Albizia lebbek, Alhagi maurorum, Aloe vera, Amelanchier ovalis, Anacardium occidentale, Anchomanes difforms, Annona squamosal, Apium graveolens, Araujia sericifera, Astragalus siculus, Baphia nitida, Berlinia grandiflora, Brassica rapa, Buddleja cordata, Bupleurum chinense, Cadia rubra, Caesalpinia ferrea, Calotropis procera, Cannabis sativa, Canthium parviflorum, Caralluma tuberculata, Carthamus tinctorius, Cedrus deodara, Celastrus paniculatus, Centella asiatica, Chasmanthera dependens, Chelidonium majus, Chrozophora verbascifolia, Cinnamomum zeylanicum, Citrullus colocynthis, Clematis chinensis, Cleome viscose, Clerodendrum infortunatum, Clitoria ternatea, Cocculus pendulus, Commiphora molmol, Cordia francisci, Cordia martinicensis, Cordia myxa, Cordia ulmifolia, Cucumis trigonus, Culcitium canascens, Curcuma zedoaria, Cuscuta chinensis, Cyathea nilgirensis, Cymbopogon schoenanthus, Cystoseira usneoides, Datisca cannabina, Desmodium canadense, Dioclea grandiflora, Diodia scandens, Dolichos falcatus, Ducrosia ismaelis, Egletes viscosa, Elaeagnus kologa, Elaeocarpus canitrus, Eriobotrya bengalensis, Ervatamia coronaria, Eryngium foetidum, Eucaluptus camaldulensis, Euphorbia hirta, Fagraea racemosa, Ficus glomerata, Foeniculum vulgare, Ganoderma lucidum, Genista patens, Glaucium flavum, Harpagophytum procumbens, Hedera rhombea, Heracleum hemsleyanum, Hibiscus sabdariffa, Himanthalia helongata, Himulus lupulus, Hypericum calycinum, Hypericum perforatum, Inula crithmoides, Inula viscosa, Ipomoea leari, Irvingia gabonensis, Juniperus oxycedrus, Laminaria achroleuca, Lantana camara, Lawsonia inermis, Ledebouriella seseloides, Lepidium sativum, Leucas aspera, Leucojum aestivum, Ligusticum sinense, Lippia alba, Lippia geminate, Luvunga scandens, Lycopodium clavatum, Lysimachia christinae, Maesa ramentacea, Melaleuca elliptica, Melaleuca styphelioides, Mentha piperita, Mikania cordata, Morinda citrifolia, Morus alba, Mucuna pruriens, Myrica nagi, Myrtus communis, Nepeta caesarea, Nepeta italica, Neurolaena lobata, Nigella sativa, Nyctanthes arbor-tristis, Ocimum sanctum, Oplopanax elatus, Origanum onites, Paeonia moutan, Panax ginseng, Pancratium maritimum, Paullinia cupana, Peganum harmala, Persea Americana, Photinia serrulata, Phyla nodiflora, Phyllanthus niruri, Phyllanthus sellowianus, Phyllanthus tenellus, Phyllanthus urinaria, Pimpinella anisum, Pinus koraiensis, Piper abutiloides, Piper cincinnatoris, Piper lindbergii, Piper longum, Piper methysticum, Piper umbellatum, Piscidia erythrina, Platycodon grandiflorum, Polygala cyparissias, Polypodium vulgare, Pongamia pinnata, Portulaca grandiflora, Portulaca oleracea, Prunus spinosa, Psammosilene tunicoides, Psidium pohlianum, Psychotria brachypodia, Psychotria colorata, Pterocarpus indicus—Ptychopetalum olacoides, Pycnocomon rutaefolia, Quercus infectoria, Quercus lineata, Randia siamensis, Ranunculus japonicas, Rhamnus procumbens, Rhazya stricta, Ricinus communis, Roylea elegans, Salvia haematodes, Santolina chamaecyparissus, Saussurea involucrate, Scabiosa atropurpurea, Senna italic, Serjania communis, Sida cordifolia, Sideritis mugronensis, Siphocampylus verticillatus, Stephania dinklagei, Stefania wightli, Strychnos nux-vomica, Synedrella nodiflora, Tabebuia chrysotricha, Tabernaemontana pandacaqui, Tamarix milotica, Taraxacum officinale, Teclea nobilis, Tecomella undulate, Teucrium carthaginense, Theobroma leiocarpa, Thymus vulgaris, Tillandsia usneoides, Tinospora cordifolia, Tinospora crispa, Torresea cearensis, Trachelospermum jasminoides, Trema guineensis, Trianthema portulacastrum, Tribulus terrestris, Trichilia catigua, Trigonella anguina, Trigonella foenum-graecum, Typhonium giganteum, Urtica dioica, Valeriana jatamansi, Vernonia condensate, Viola mandshurica, Vitex negundo, Zingiber officinale*, and *Ziziphus jujube*.

The dissolution-limited embodiments of the present disclosure may involve the use of a solid active ingredient as the active compound. One skilled in the art will recognize that, in many cases, the individual purified components of essential oils are often solids near ambient (room) temperature. For example, the liquid known as peppermint essential oil has as its predominant component menthol, which is a solid at room temperature. Menthol typically constitutes 50% to 80% of peppermint oil. As a further example, in a case where peppermint oil includes 70% menthol, the menthol component is accompanied by 30% of "other ingredients." One of ordinary skill will understand that these other components are generally quite similar in molecular structure to menthol, but different enough that these minor ingredients act to lower the melting point of the menthol. One of ordinary skill in the art would further understand that this melting point depression effect can be common in plant oils, and means that many of the benefits from essential oils discussed in this disclosure can in fact be achieved by solid actives, which are suited for the yarns and other substrates disclosed herein.

Fungal infections of the skin can be notoriously long-lasting, and compliance with an antifungal spray can be poor, for example, due to the need for daily application in the harried early morning time. An antifungal-medicated piece of clothing that is washable could provide for long-term application to the site of infection without requiring any compliance on the part of the user, beyond the normal washing of the fabric that is required in any case. With, for example, 4 or 5 pairs of medicated socks, one could maintain continuous application of the active to the site during all waking hours of the day, and even at night if desired, without any conscious effort other than donning the designated socks each morning.

Vapor-releasing salves can be notoriously short-acting, and are not well suited for constancy of release. On the other hand, prior known patches are unsightly and even disfiguring. The embodiments of the present disclosure can overcome these drawbacks by providing a sufficiently sophisticated delivery system for constancy of release which is nevertheless in the format of a fully functional (e.g., washable) article of clothing, such as a scarf, cap, veil, woven necklace, choker, neck band, ear muffs, or other headwear. Other applications that may benefit from vapor release include trigeminal neuropathy, also known as "the suicide disease" due to the excruciating pain it causes. This condition can be treated, for example, by using a delivery system disclosed herein that releases pain-numbing vapors such as menthol at a more constant rate than salves without requiring repeated applications every few hours. Other conditions possibly treatable with such an approach include nasal congestion, emphysema, sarcoidosis, pleural effusion, pulmonary edema, pulmonary hypertension, pneumonia, tuberculosis, various infectious diseases, respiratory irritation (e.g., from breathing polluted air), and non-productive coughing.

Nutritional and nutraceutical compounds may also be delivered transdermally according to embodiments of the present disclosure. Such compounds may be delivered, e.g., via a transdermal patch or via everyday-use and other fabrics. Moreover, the large surface areas for transdermal delivery made possible by the delivery systems disclosed herein could allow for delivery of larger doses than would be possible for traditional transdermal patches.

Considerable instruction has been provided herein for producing washable, medicated materials for delivery of drug to the skin, which with many drugs translates into systemic delivery (i.e., transdermal delivery to the bloodstream). Nicotine, fentanyl, methylphenidate, scopolamine, nitroglycerine, rivastigmine, clonidine, Vitamin B12, estrogen and testosterone are some examples of drugs that are currently delivered transdermally through medicated patches, which are, of course, not washable, and thus must be discarded when dirty. Drugs requiring daily (or near-daily) application could benefit from the embodiments described herein; for example, with children's ADHD, exposure to dirt of all forms is of course to be expected for a (hyperactive) child, and a washable, reusable patch could be an advantage. Furthermore, if the present disclosure is used in the form of an article of clothing, particularly one that is fairly tight-fitting such as a sock or cap, then it becomes possible to eliminate the need for adhesives, which are essentially required for traditional transdermal patches and present a range of practical issues. The embodiments described herein could also be used to deliver drugs systemically through mucosal membranes—a route known as transmucosal.

In some embodiments, resiniferatoxin, and related materials containing components of greater than 1 billion Scoville units, including extracts of *Euphorbia* species such as *Euphorbia resinifera* or *Euphorbia poissonii*, can be used as active compounds. Such compounds can be used in treating pain and/or other conditions.

It is within the scope of this disclosure for the "active" to be one that improves the quality of life through the steady release, even through many washes, of a pleasant and social aroma, including pheromones. The designs discussed elsewhere herein for promoting release into the air (discussed above in relation to inhalation-based delivery) could be used for such an application. Many of the essential oils listed and discussed herein are well established as pleasing aromas or even as perfume components. Some embodiments discussed herein that yield a more nearly-constant release rate could be used to create textiles, such as dresses and scarfs, which do not suffer from the relatively short action of a single application (spray) of perfume, and in fact do not require any action on the part of the customer or user.

Delivery of drugs and even some nutritional supplements to infants and toddlers can be a challenge due to swallowing/coordination limitations and taste intolerance. The delivery systems disclosed herein provide convenient products and methods for overcoming these delivery challenges, by incorporating medicament- or supplement-releasing embodiments of the disclosure into and onto commonly used (and frequently washed) items such as pacifiers, milk/formula bottles, stuffed animals, etc. Hydrophobic actives, in particular, will in general be released more rapidly into milk or formula than into water, and milk, particularly flavored milk, can mask the taste of medicaments, providing for relatively high dilutions without increasing total fluid intake.

In another embodiment, gloves releasing circulation-improving compounds or oils (e.g., vasodilatory, rubifacient) and/or local anesthetic compounds for treatment or prevention of Raynaud's disease and related conditions may be provided.

Certain embodiments also provide athletic garments and undergarments and other sportswear/active wear releasing one or more of the following: performance-enhancing actives; aspirin, local anesthetic and/or capsaicin for relief of pain or cold; creatine, glutamine, citrulline malate, beta-alanine, branched-chain amino acids, for muscle recovery or muscle stimulation; and handkerchiefs releasing cologne or perfume, antimicrobials, and/or vitamins.

In various embodiments, the polymeric coating/imbibition and/or the polymeric/protective matrix can be formed in situ through the use of curable monomers. Curable monomer blends, including multi-functional monomers for cross-linking, can be formed in which the one or more actives (e.g., a solution or dispersion of actives) are in turn dissolved or dispersed to form a monomer mixture. The solution or dispersion of actives and/or the monomer blend can also incorporate a free radical initiator or catalyst to form a curable monomer resin system (also referred to herein as a "monomer resin system"). The solution or dispersion of active, the monomer blend, and/or the curable monomer resin system may be polymerized to form a polymer or polymer coating having a glass transition temperature ($T_g$) that enables the polymer or polymer coating to be ductile and not brittle so as to aid or facilitate further processing of the drug delivery system (e.g., knitting into fabric) and/or to maintain the integrity of the drug delivery system. In certain embodiments, the $T_g$ may be selected from a range of between about −60° C. and about 110° C. In some embodiments, the $T_g$ may be selected from a range of between about −30° C. and about 30° C. In particular embodiments, the $T_g$ may be selected from a range of between about −20° C. and about 20° C.

The free radical initiator or catalyst can aid in polymerizing the monomer mixture and/or the monomer resin system in situ on the yarn, fiber, or substrate. Such monomer resin systems can employ photosensitive initiators for this purpose such that the coating and/or the imbibition can be polymerized, cured, and/or cross-linked using ultraviolet light. In some embodiments, the monomer resin systems may be passed through a light box (also referred to herein as a "reflective chamber" or "curing chamber"). The light box can provide or emit the ultraviolet light. In certain embodiments, the light box contains UV-LED lights that deliver ultraviolet light at specific wavelength(s) and/or intensity to activate the photo-active initiator in the mixture to polymerize the coating. The light box may also provide a controlled environment, e.g., including one or more inert gases (e.g., nitrogen).

In some embodiments, the monomer resin system may be applied to or disposed on a single filament yarn such that the single filament yarn is coated with the monomer resin system. In certain embodiments, the monomer resin system may be applied to, disposed on, or incorporated into a multiple filament yarn (i.e., a yarn including a plurality of single filaments). The monomer resin system can coat and/or be imbibed into the multiple filament yarn. Stated another way, the monomer resin system can coat or cover at least a portion of an outside surface of the multiple filament yarn and/or the monomer resin system can be imbibed or soaked up by the multiple filament yarn such that at least a portion of the monomer resin system is disposed in the interstices of or spaces between the plurality of single filaments that make up the multiple filament yarn. In various embodiments, a single filament yarn and/or a multiple filament yarn can be treated with a monomer resin system to form a drug delivery system.

The resultant monomer resin system can be transferred to a coating line or application line for delivery to a yarn, fabric, or substrate. The monomer resin system can be applied to a finish tip, which, when wetted by the monomer resin system, transfers liquid material to the surface of yarn or fiber as it passes over. In certain embodiments, the monomer resin system treated or resultant treated fiber or yarn can then pass through a curing chamber or light box including a series of UV LED lights tuned to the wavelength of the initiator to activate the initiator. Other lighting sources are also within the scope of this disclosure.

One aspect of the present disclosure is related to methods for making or manufacturing a drug delivery system. The methods can include forming a solution comprising a monomer, an initiator, and/or an active compound. The methods can also include applying or disposing the solution on a substrate, wherein the substrate comprises at least one of a yarn, a yarn precursor, a thread, a filament, a fiber, and/or another suitable substrate. In some embodiments, the methods may include exposing the solution and the substrate to UV light to initiate polymerization and/or cross-linking of the solution. The solution may further include an oligomer and/or any other suitable material or component.

Another aspect of the present disclosure is related to drug delivery systems. The drug delivery systems may be prepared by a process including the step of forming or preparing a solution including a monomer, an initiator, and/or an active compound. The process can also include the step of applying or disposing the solution on a substrate, wherein the substrate comprises at least one of a yarn, a yarn precursor, a thread, a filament, a fiber, and/or another suitable substrate. In certain embodiments, the process can include the step of exposing the solution and the substrate to UV light to initiate polymerization and/or cross-linking of the solution. The solution may further include an oligomer and/or any other suitable material or component.

In some embodiments, when multiple filament yarns, and particularly yarns of plant or animal source or bulked yarns, are passed through reservoirs containing a solution including a monomer, an initiator, and/or an active compound, they may spontaneously absorb or imbibe this solution. The solution may further include an oligomer and/or any other suitable material or component.

In other embodiments, when multiple filament yarns, and particularly yarns of plant or animal source or bulked yarns, are passed through reservoirs containing polymers (e.g., elastomers), RTV, or other (hydrophobic) matrix polymer precursor fluid, they may spontaneously absorb or imbibe this fluid. Furthermore, the active compounds (e.g., active crystals) dispersed in this fluid may also generally be imbibed by the substrate yarn.

When coating and/or imbibing a yarn or substrate, there is a continuum of processing schemes that may be best delineated by the following well-defined reference points: yarn-level coating and/or imbibition, wherein individual yarns are coated and/or imbibed; warp coating and/or imbibition, wherein in a weaving process the yarns or fibers making up the "warp" are coated and/or imbibed; weft coating and/or imbibition, wherein in a weaving process the yarns or fibers making up the "weft" are coated and/or imbibed; and textile-level coating and/or imbibition, wherein a two-dimensional textile or fabric is coated and/or imbibed.

Advantages of textile-level coating and/or imbibition are well-known to one skilled in the art. Entire two-dimensional textiles and fabrics can be coating and/or imbibed in one unit operation. There are very strong reasons for doing the coating and/or imbibition step at the textile level. Metering devices can be used to control the rate of coating and/or imbibing onto the yarn. The wicking devices have easy screws to control the tension on the yarn, thereby allowing for greater control over how much matrix is coated onto and/or imbibed into the yarn. Wicking/oiling devices, ceramic guides and finish applicators also may be used to apply the drug/matrix to the yarn.

Generally, fibers and yarns found in garments come from either natural sources (e.g., silk, cotton, etc.) or synthetic (e.g., nylon, polyester, acetates, etc.). The selection of material type, fiber type, and mixture in a garment construction may determine a number of factors for consumer benefit, use, and desire. Likewise, the method of construction (e.g., knitting, weaving, sewing, etc.) may also determine at least a portion of the final attributes. Additionally, fibers, yarns, and finished garments can be further processed or treated to create additional benefit.

One such method is fiber wrapping or covering. In certain embodiments, the yarn or substrate may need greater elasticity or stretch. Thus, the yarn (i.e., a primary yarn) may be plied or twisted with an air-covered yarn (i.e., a secondary yarn), such as spandex, to enable additional stretch of the yarn. In some embodiments, the secondary yarn, which wraps, coils, or covers the primary yarn, may be hydrophobic or hydrophilic. Additionally, the yarn may be air-covered/air-intermingled (i.e., blowing air onto the yarn and adding a spandex core into the middle of the yarn). These methods may be useful for garments that need a lot of stretch, e.g., such as tights or leggings (or even the elastic portion at the top of a sock).

Semi-finished garments and articles of wear can be further treated through methods of finishing, treating, washing, dyeing, etc. For example, socks can be boarded, steamed, and sized to fix the shape. Articles of wear are also often pre-washed to either remove excess dye or to soften the surface or appearance. Accordingly, in some embodiments, the coating and incorporated active may need to be resilient throughout the formation of a garment and/or post-treatments. Accordingly, the coating may be flexible with abrasion resistance, be able to withstand sharp angles and points of frictional contact so as to avoid cracking or flaking, be able to withstand processing temperatures, and have similar flexural properties to that of the fiber or yarn to move in concert with the fiber or yarn during deformation (e.g., stretching or folding).

Garments containing active fibers can be tested in various ways for efficacy, e.g., measurement of active release and/or resistance to active loss by use, wear, application, and/or laundering can be performed. For example, a solvent extraction method on a basic, coated yarn or final garment can be conducted. While the use of water or synthetic sebum/sweat can be used, so too can basic solvents that accelerate potential active release. Accelerating release can allow for faster, correlated analysis to be done and can be geared towards working with a solvent that solubilizes the active. The extract arising from such extractions can then be characterized, e.g., by HPLC to determine the quantity of active released based on the time and conditions of extraction. As to studying resistance to laundering, fibers, yarns, and garments can be washed under controlled conditions and time (e.g., cycles) followed by an extraction as discussed above. Comparison of extraction data before and after laundering can be used to determine the quantity of active lost.

The selection of monomers in a curable system or the selection of a pre-made polymer coating can be varied to enhance necessary functions including, but not limited to: coupling to the substrate (e.g., yarn, fiber, etc.); compatibility with and/or the release profile of the active; physical and/or mechanical properties to aid garment creation (e.g., knitting); and/or to manage the tactile and other aesthetics of the yarns, fibers, or other substrates.

In some embodiments, a monofunctional monomer may be used. For example, an alkyl methacrylate having an alkyl group having between one and 12 carbon atoms may be used. Such an alkyl methacrylate monomer may be selected from at least one of methyl methacrylate, ethyl methacrylate, n-propyl methacrylate, isopropyl methacrylate, n-butyl methacrylate, t-butyl methacrylate, sec-butyl methacrylate, pentyl methacrylate, 2-ethylhexyl methacrylate, 2-ethylbutyl methacrylate, n-octyl methacrylate, isobornyl methacrylate, isooctyl methacrylate, isononyl methacrylate, and/or lauryl methacrylate. The alkyl methacrylate monomer may be used alone or in combination (e.g., at least two alkyl methacrylate monomers may be used) to ensure the glass transition temperature. In another example, an alkyl acrylate having an alkyl group having between one and 12 carbon atoms may be used. Such an alkyl acrylate monomer may be selected from at least one of methyl acrylate, ethyl acrylate, n-propyl acrylate, isopropyl acrylate, n-butyl acrylate, t-butyl acrylate, sec-butyl acrylate, pentyl acrylate, 2-ethylhexyl acrylate, 2-ethylbutyl acrylate, n-octyl acrylate, isobornyl acrylate, isooctyl acrylate, isononyl acrylate, and/or lauryl acrylate. The alkyl acrylate monomer may be used alone or in combination to ensure the glass transition temperature. Other suitable monofunctional monomers are also within the scope of this disclosure.

In certain embodiments an aromatic acrylate or an aromatic methacrylate may be used. For example, the aromatic acrylate or methacrylate may be selected from at least one of phenyl acrylate/methacrylate, phenylethyl acrylate/methacrylate, and/or phenoxyethyl acrylate/methacrylate. Other suitable aromatic acrylates or methacrylates are also within the scope of this disclosure.

In various embodiments, a hydroxy-containing acrylate or a hydroxy-containing methacrylate may be used. The hydroxy-containing acrylate or methacrylate may be selected from at least one of a hydroxyalkyl acrylate/methacrylate (e.g., 2-hydroxyethyl acrylate/methacrylate), 2-hydroxypropyl acrylate/methacrylate, 4-hydroxybutyl acrylate/methacrylate, 6-hydroxyhexyl acrylate/methacrylate, and/or 8-hydroxyoctyl acrylate/methacrylate. Other suitable hydroxy-containing acrylates or methacrylates are also within the scope of this disclosure.

In some embodiments, the acrylate or methacrylate may be selected from at least one of 2(2-ethoxyethoxy) ethyl acrylate; 2-phenoxyethyl acrylate; 3,3,5 trimethylcyclohexyl methacrylate; acrylate ester; acrylic ester; acrylic monomer; alkoxylated lauryl acrylate; alkoxylated phenol acrylate; alkoxylated tetrahydrofurfuryl acrylate; aromatic acrylate monomer; C12 C14 alkyl methacrylate; caprolactone acrylate; cyclic trimethylolpropane formal acrylate; cycloaliphatic acrylate monomer; dicyclopentadienyl methacrylate; diethylene glycol methyl ether methacrylate; ethoxylated (4) nonyl phenol acrylate; isobornyl acrylate; isobornyl methacrylate; isodecyl acrylate; isodecyl methacrylate; isooctyl acrylate; lauryl acrylate; lauryl methacrylate; methoxy polyethylene glycol (350) monoacrylate; methoxy polyethylene glycol (350) monomethacrylate; methoxy polyethylene glycol (550) monoacrylate; methoxy polyethylene glycol (550) monomethacrylate; octyldecyl acrylate; stearyl acrylate; stearyl methacrylate; tetrahydrofurfuryl acrylate; tetrahydrofurfuryl methacrylate; tridecyl acrylate; tridecyl methacrylate; and/or triethylene glycol ethyl ether methacrylate.

In certain embodiments, cross-linkable, multi-functional acrylates and methacrylates may be used. For example, a difunctional monomer may be used, wherein the difunctional monomer is selected from at least one of 1,12 dodecanediol dimethacrylate; 1,3-butylene glycol diacrylate; 1,3-butylene glycol dimethacrylate; 1,3-butylene glycol dimethacrylate; 1,4-butanediol diacrylate; 1,4-butanediol dimethacrylate; 1,6 hexanediol diacrylate; 1,6 hexanediol dimethacrylate; acrylate ester; alkoxylated aliphatic diacrylate; alkoxylated hexanediol diacrylate; alkoxylated hexanediol diacrylate; alkoxylated hexanediol diacrylate; alkoxylated hexanediol diacrylate; alkoxylated neopentyl glycol diacrylate; cyclohexane dimethanol diacrylate; cyclohexane dimethanol dimethacrylate; diethylene glycol diacrylate; diethylene glycol dimethacrylate; dipropylene glycol diacrylate; dipropylene glycol diacrylate; ethoxylated (10) bisphenol A diacrylate; ethoxylated (2) bisphenol A dimethacrylate; ethoxylated (3) bisphenol A diacrylate; ethoxylated (30) bisphenol A diacrylate; ethoxylated (30) bisphenol A dimethacrylate; ethoxylated (4) bisphenol A diacrylate; ethoxylated (4) bisphenol A dimethacrylate; ethoxylated (8) bisphenol A dimethacrylate; ethoxylated bisphenol A dimethacrylate; ethoxylated bisphenol A dimethacrylate; ethoxylated(10) bisphenol dimethacrylate; ethoxylated (6) bisphenol A dimethacrylate; ethylene glycol dimethacrylate; neopentyl glycol diacrylate; neopentyl glycol dimethacrylate; polyethylene glycol (200) diacrylate; polyethylene glycol (400) diacrylate; polyethylene glycol (600) diacrylate; polyethylene glycol (600) dimethacrylate; polyethylene glycol dimethacrylate; polyethylene glycol dimethacrylate water solution; polypropylene glycol (400) dimethacrylate; propoxylated (2) neopentyl glycol diacrylate; tetraethylene glycol diacrylate; tetraethylene glycol dimethacrylate; tricyclodecane dimethanol diacrylate; triethylene glycol diacrylate; triethylene glycol dimethacrylate; and/or tripropylene glycol diacrylate. In another example, a tetra (or higher) functional monomer may be used, wherein the tetra (or higher) functional monomer is selected from at least one of di-trimethylolpropane tetraacrylate, dipentaerythritol pentaacrylate, ethoxylated (4) pentaerythritol tetraacrylate, low migration alkoxylated pentaerythritol tetraacrylate, low viscosity dipentaerythritol pentaacrylate, pentaacrylate ester, and/or pentaerythritol tetraacrylate. Other cross-linkable, multi-functional acrylates and methacrylates are also within the scope of this disclosure.

In various embodiments, an oligomer may be used. Suitable oligomers include, but are not limited to, epoxy acrylates, urethane acrylates, SARBOX® carboxylic acid half esters, polyester acrylates, acrylated acrylics, and/or low viscosity oligomers. For example, the oligomer may be selected from at least one of acrylate stabilizing additive, acrylated acrylic, adhesion promoting oligomer, aliphatic urethane acrylates, allylic oligomers, amine modified acrylate oligomers, aromatic urethane acrylates, chlorinated polyester acrylate oligomers, epoxy acrylates, epoxy methacrylates, fatty acid-modified acrylate oligomers, hydrophobic oligomers, laminating adhesive resins, low viscosity oligomers, melamine acrylate, polyester acrylate oligomers, pressure sensitive adhesive resins, silicone acrylate oligomers, urethane methacrylates, and/or UV curable resins. Other suitable oligomers are also within the scope of this disclosure.

In some embodiments, a polyurethane acrylate system may be used. For example, the polyurethane acrylate system may be selected from at least one of aliphatic urethane acrylate; aliphatic urethane acrylate oligomer; aliphatic urethane diacrylate oligomer with acrylate monomer diluent; aliphatic urethane oligomer; dual cure urethane acrylate oligomer; high elongation urethane acrylate; hydrophobic aliphatic urethane acrylate; trifunctional urethane acrylate; trifunctional urethane acrylate blended with tripropylene glycol diacrylate; urethane acrylate; urethane acrylate blend; urethane acrylate blended with 1,6 hexanediol diacrylate; urethane acrylate blended with 2(2-ethoxyethoxy) ethyl acrylate; urethane acrylate blended with tripropylene glycol diacrylate; urethane acrylate blended with ethoxylated (3) trimethylolpropane triacrylate; urethane acrylate blended with isobornyl acrylate; and/or urethane acrylate oligomer (e.g., siliconized urethane acrylate oligomer). Other suitable polyurethane acrylate systems are also within the scope of this disclosure.

The monomer or oligomer may also be selected from at least one of, aliphatic silicone acrylate, LED cure promoting oligomer, urethane dimethacrylate, and/or any other suitable monomer or oligomer.

Certain embodiments of the disclosure rely substantially, or even entirely, on the release characteristics of the polymer matrix that is in direct contact with the active. As described above, the embodiments described herein may include solid active (e.g., crystalline active, active powders, etc.) dispersed in a polymeric matrix, and configured such that the egress of active from the matrix is substantially limited by the appropriate shape and coating of the polymeric matrix, so as to achieve a near-constant rate of active release over an extended period of time.

As discussed above, monomers may be selected based meeting a variety of criteria including, but not limited to: compatibility with the active, control of hydrophobicity, specific ability to cross-link via multi-functionality, viscosity for pumping coating, wettability and potential adhesion to the yarn or substrate, etc. The monomer blend can also include a free radical initiator which may be a UV-activated initiator to allow for UV-curing of the coating. Such initiators are aligned with specific light source wavelengths. The oligomer/monomer components are often warmed (e.g., between about 25° C. and about 50° C.) to enhance mixing followed by initiator and then incorporation of the actives to form a stable solution or dispersion.

The various embodiments of the present disclosure can include or utilize polymers, prepared in situ on the yarn, fiber, or substrate or coated and/or imbibed from solution, thus forming a functional coating, which serves as a protective matrix for beneficial actives and in which, in turn, controls their delivery. In certain embodiments, the polymer may be hydrophobic and/or cross-linked. Cross-linking (also referred to as "curing," "vulcanizing," and "thermosetting") applied to a dispersion or suspension of active particles in a polymer, oligomer, or monomer matrix, commercial coating or adhesive, chemically reactive linear polymer, etc.—can be employed by the various embodiments of the present disclosure for preparing yarns, textiles, and fabrics that can protect the beneficial active against excessive loss during laundering, as well as against a wide range of chemical degradation reactions including hydrolysis, oxidation, acid/base-catalyzed reactions, etc. The polymer matrices can be formed from various polymer- or oligomer-based systems, including commercially available elastomeric adhesives, glues, coatings, caulks, sealants, casting materials, curable monomers and cross-linking systems. The various embodiments of the present disclosure can also be formed from one or more monomers and or polymers in any combination.

A reactive coating and/or imbibition blend can be continuously or substantially continuously pumped by a positive displacement pump ("peristaltic pump") from a reservoir and deposited onto a yarn through an orifice in contact with a moving threadline. The yarn can pass into a reflective chamber or light box with a UV-transparent window through which it is radiated by UV light source optimized for the selected photo-initiator. The interior of the reflective chamber can be inerted by constant flow of inert gas, such as nitrogen, to reduce or eliminate the presence of oxygen.

In some embodiments, after the polymerization of the dispersion or suspension of active particles in a polymer, oligomer, or monomer matrix on the yarn or textile, the yarn or textile may be rewound into a bundle such as a ball, skein, hank, cone, or cake for later use in the knitting of garments.

In specific embodiments, the functional coating demonstrates that the polymers may be used as a vehicle to load one or more actives into and/or onto the yarn, yarn precursor, thread, filament, fiber, or other substrate and/or immobilize the one or more actives in and/or on the yarn, yarn precursor, thread, filament, fiber, or other substrate. For example, in particular embodiments, one or more actives is combined with a polymer or mixed into a curable monomer system to form a mixture or solution, which is coated on and/or imbibed by a yarn, yarn precursor, thread, filament, fiber, or substrate. In some embodiments, the polymerization occurs in the presence of the dispersed, dissolved, or suspended active particles, resulting in a configuration in which local stresses and strains on the polymer associated with "forcing" solid active particles into an already-cross-linked polymer are minimized or eliminated. In specific embodiments, the polymer may be cross-linked. Such strains, at least at high active loadings, can lead to higher permeability and loss of active-protecting effect. Entry of solid active particles (e.g., crystals) into, or formation inside, a previously cross-linked polymeric core can also cause distortion of the structure, leaving the active accessible when the purpose of encapsulation is to make it inaccessible. In other embodiments, however, all or a portion of the cross-linking can occur prior to introduction of the active.

In certain embodiments, solid active particles or powders (e.g., crystalline active particles) are used. Solid active particles (e.g., crystalline active particles) may be used, in part, to better achieve dissolution-limited release kinetics. Exemplary forms of active compounds that can be used include, but are not limited to, crystalline or polycrystalline solid particles, semi-crystalline solid particles, amorphous solid particles, plant extracts comprising crystalline or amorphous solid domains of one or more active compounds from the plant, and mixtures or combinations thereof. In further embodiments, the active compounds may include components or fractions of plant essential oils, may be crystalline at room temperature, and suitable for use. The term "plant essential oils" is as described in U.S. Patent Application Publication No. 2014/0271863, which is incorporated herein by reference in its entirety and which also provides a listing of some of the organic compounds that may be responsible for the desirable or therapeutic effects of these oils.

Some of the embodiments disclosed herein include crosslinking so as to lock, hold, or otherwise temporarily retain active particles or their conjugates in place and protect them from degradation and premature loss, particularly in the face of stress conditions such as those encountered in laundering.

Importantly, long-term use of a dermal or transdermal approach may be employed without engendering the risks or downsides of occlusive and/or adherent patches or bandages. Certain areas of the body may be well-suited to delivery of an active substance via clothing, but not well-suited to more traditional methods of delivery. For example, the feet or hands may be particularly well-suited to delivery via socks or gloves, whereas other topical delivery methods known in the art may not provide as efficient delivery because of the risk of being rubbed off, etc. Further, current fabric-based products of purported medicinal value, such as diabetic socks for example, which have not been provided with the obvious medicaments due to washing requirements, can now be medicated and yet still remain fully washable.

In some embodiments, the active may include a heating or cooling active. For example, the active may be selected from at least one of menthol, a menthol derivative, WS compounds (Wilkinson Sword™) such as WS-3, 5, 12, and 23, methyl salicylate, ethyl salicylate, trolamine salicylate, capsaicin, a synthetic heating or cooling agent (e.g., nonivamide), vanillyl butyl ether, ginger, eugenol, kunzea, arnica, camphor, niacinamide, and/or diphenyl hydramine. In certain embodiments, the active may include a cooling component blend (e.g., isopulegol, menthyl lactate, menthoxypropanediol, and 2-isopropyl-N,2,3-trimethylbutyramide (WS-23). Other suitable heating or cooling actives are also within the scope of this disclosure.

In various embodiments, the active may include an anti-fungal active. For example, the active may be selected from at least one of clotrimazole, miconazole, ketoconazole, terbinafine, fluconazole, and/or amphotericin. Other suitable anti-fungal actives are also within the scope of this disclosure.

In some embodiments, the active may include an antipruritic and/or skin calming active. For example, the active may be selected from at least one of an antihistamine (e.g., diphenhydramine or hydroxyzine), a corticosteroid (e.g., hydrocortisone), a counterirritant (e.g., mint oil, menthol, or camphor), and/or a local anesthetic (e.g., lidocaine, pramoxine, benzocaine, trolamine, calamine, coenzyme Q-10, or diphenyl hydramine). Other suitable antipruritic and/or skin calming actives are also within the scope of this disclosure.

In certain embodiments, the active may include an acne-treating active. For example, the active may be selected from at least one of an alpha-hydroxy acid (AHA) (e.g., glycolic acid or lactic acid), benzoyl peroxide, clay, salicylic acid, sulfur, tea-tree oil, azelaic acid, topical retinoid, and/or kojic acid. Other suitable acne-treating actives are also within the scope of this disclosure.

In various embodiments, the active may include an emollient. The emollient may be selected from at least one of shea butter, cocoa butter, a castor oil derivative, lanolin, squalene, coconut, jojoba, sesame, almond, another plant oil and/or butter, cetyl alcohol and derivatives, and/or a stearate. Other suitable emollients are also within the scope of this disclosure.

Other suitable actives include, but are not limited to, cannabidiol, BEAUPLEX® VH; ALL-Q® (coenzyme Q10) plus; coenzyme, SPECIKARE™ CQ10; ROVISOME™ Q10; SIGNALINE™ S, SERENITYL™ BIOFUNCTIONAL; ATPEPTIDE™ IS; PROLIPID™ 141; VITAL ET™; GENTI-FOL® SA; CELLULINO®; lidocaine; SHAPEPERFECTION™; FRESH'IN™; CC menthol 50% (CYCLOSYSTEM COMPLEX®); CARNIPURE™ CRYSTALLINE; SYNIORAGE™ LS 9847; ULTRA FILLING SPHERES™; RONACARE® nicotinamide; VEXEL™ SP; cafeisilane C; ROVISOME™ caffeine; ISOCELL™ SLIM; DISILANOL C+™; SYNIORAGE™ LS 9847, N,N-Diethyl-meta-toluamide (DEET), picaridin, and/or melatonin. Other suitable actives are also within the scope of this disclosure (see, e.g., Table 2).

TABLE 2

| Skin Sensations | Skin Calming | Skin Energizing/Renewal | Skin Firming |
|---|---|---|---|
| Heat | Acne | Hydration | Anti-wrinkles |
| Cool | Irritation | Cellular Energy | Cellulite |
| Odor, Itch | Rosacea/Psoriasis | Protection | Anti-Glycation |
| Capsaicin | Emollients | Vitamins A, C and E | Carnosine |
| Nonivamide | Lidocaine | Glycolic Acid+ | Carnitine |
| Menthol | CoQ-10 | Resveratrol | Vitamin B's, E & C |
| WS Derivatives | Cinnamates | Polyphenols | Peptides |
| Miconazole | Piroctone Olamine | Niacinamide | Salicylates |
| Diphenhydramine | Calamine | Glycyrrhizinic Acid+ | Alpha hydroxyl acids |
| | | Ergothioneine | |
| | | Ferulic Acid | |
| | | Caffeine | |

The dissolution-limited embodiments of the present disclosure may involve the use of a solid active ingredient as the active compound. One skilled in the art will recognize that, in many cases, the individual purified components of essential oils are often solids near ambient (room) temperature. For example, the liquid known as peppermint essential oil has as its predominant component menthol, which is a solid at room temperature. Menthol typically constitutes 50% to 80% of peppermint oil. As a further example, in a case where peppermint oil includes 70% menthol, the menthol component is accompanied by 30% of "other ingredients." One of ordinary skill will understand that these other components are generally quite similar in molecular structure to menthol, but different enough that these minor ingredients act to lower the melting point of the menthol. One of ordinary skill in the art would further understand that this melting point depression effect can be common in plant oils, and means that many of the benefits from essential oils discussed in this disclosure can in fact be achieved by solid actives, which are suited for the yarns and other substrates disclosed herein.

Fungal infections of the skin can be notoriously long-lasting, and compliance with an antifungal spray can be poor, for example, due to the need for daily application in the harried early morning time. An antifungal-medicated piece of clothing that is washable could provide for long-term application to the site of infection without requiring any compliance on the part of the user, beyond the normal washing of the fabric that is required in any case. With, for example, four or five pairs of medicated socks, one could maintain continuous application of the active to the site during all waking hours of the day, and even at night if desired, without any conscious effort other than donning the designated socks each morning.

Vapor-releasing salves can be notoriously short-acting, and are not well suited for constancy of release. On the other hand, prior known patches are unsightly and even disfiguring. The embodiments of the present disclosure can overcome these drawbacks by providing a sufficiently sophisticated delivery system for constancy of release which is nevertheless in the format of a fully functional (e.g., washable) article of clothing, such as a scarf, cap, veil, woven necklace, choker, neck band, ear muffs, or other headwear. Other applications that may benefit from vapor release include trigeminal neuropathy, also known as "the suicide disease" due to the excruciating pain it causes. This condition can be treated, for example, by using a delivery system disclosed herein that releases pain-numbing vapors such as menthol at a more constant rate than salves without requiring repeated applications every few hours. Other conditions possibly treatable with such an approach include nasal congestion, emphysema, sarcoidosis, pleural effusion, pulmonary edema, pulmonary hypertension, pneumonia, tuberculosis, various infectious diseases, respiratory irritation (e.g., from breathing polluted air), and non-productive coughing.

Nutritional and nutraceutical compounds may also be delivered transdermally according to embodiments of the present disclosure. Such compounds may be delivered, e.g., via a transdermal patch or via every day-use and other fabrics. Moreover, the large surface areas for transdermal delivery made possible by the delivery systems disclosed herein could allow for delivery of larger doses than would be possible for traditional transdermal patches.

Considerable instruction has been provided herein for producing washable, medicated materials for delivery of drug to the skin, which with many drugs translates into systemic delivery (i.e., transdermal delivery to the bloodstream). Nicotine, fentanyl, methylphenidate, scopolamine, nitroglycerine, rivastigmine, clonidine, vitamin B12, estrogen, and testosterone are some examples of drugs that are currently delivered transdermally through medicated patches, which are, of course, not washable, and thus must be discarded when dirty. Drugs requiring daily (or near-daily) application could benefit from the embodiments described herein; for example, with children's ADHD, exposure to dirt of all forms is of course to be expected for a (hyperactive) child, and a washable, reusable patch could be an advantage. Furthermore, if the present disclosure is used in the form of an article of clothing, particularly one that is fairly tight-fitting such as a sock or cap, then it becomes possible to eliminate the need for adhesives, which are essentially required for traditional transdermal patches and present a range of practical issues. The embodiments described herein could also be used to deliver drugs systemically through mucosal membranes—a route known as transmucosal.

In some embodiments, resiniferatoxin, and related materials containing components of greater than one billion Scoville units, including extracts of *Euphorbia* species such as *Euphorbia resinifera* or *Euphorbia poissonii*, can be used as active compounds. Such compounds can be used in treating pain and/or other conditions.

It is within the scope of this disclosure for the "active" to be one that improves the quality of life through the steady release, even though many washes, of a pleasant and social aroma, including pheromones. Many essential oils are well established as pleasing aromas or even as perfume components. Some embodiments discussed herein that yield a more nearly-constant release rate could be used to create textiles, such as dresses and scarfs, which do not suffer from the relatively short action of a single application (spray) of perfume, and in fact do not require any action on the part of the customer or user.

Delivery of drugs and even some nutritional supplements to infants and toddlers can be a challenge due to swallowing/coordination limitations and taste intolerance. The delivery systems disclosed herein provide convenient products and methods for overcoming these delivery challenges, by incorporating medicament- or supplement-releasing embodiments of the disclosure into and onto commonly used (and frequently washed) items such as pacifiers, milk/formula bottles, stuffed animals, etc. Hydrophobic actives, in particular, will in general be released more rapidly into milk or formula than into water, and milk, particularly flavored milk, can mask the taste of medicaments, providing for relatively high dilutions without increasing total fluid intake.

Certain embodiments also provide athletic garments and undergarments and other sportswear/active wear releasing one or more of the following: performance-enhancing actives; aspirin, local anesthetic and/or capsaicin for relief of pain or cold; creatine, glutamine, citrulline malate, beta-alanine, branched-chain amino acids, for muscle recovery or muscle stimulation; and handkerchiefs releasing cologne or perfume, antimicrobials, and/or vitamins.

In one embodiment related to wound dressing, a delivery system of the present disclosure may be used as an insert or lining to a cast, splint, sling or brace. There are over 6.8 million broken bones in the U.S. every year, many requiring the use of a cast, splint, sling, or brace for treatment. In the case of individuals treated for scoliosis, for example, patients must wear a full body cast and lie in bed for 3 to 6 months. There are many common negative issues associated with wearing casts for prolonged periods of time, including, but not limited to, allergic reactions, skin sores, infections, joint stiffness, muscle loss, offensive odor, burns, and compartment syndrome, which greatly limits blood flow. Many or all of these negative side effects could be effectively treated or mitigated by delivery of appropriate actives via the systems of the present disclosure. Such an application could employ the disclosed systems in the form of an insert or lining to a cast, splint, sling, or brace. The cast/insert system could be designed such that the insert could be removed, daily if necessary, for washing without interfering with the supportive and protective functions of the cast or brace. The insert could provide release of antimicrobials, growth factors, analgesics, and skin toning/cosmeceutical actives, and release medicaments or essential oils designed to increase blood circulation. Several classes of actives are beneficial for treatment of wounds and may be used with the systems of the present disclosure, including, but not limited to, growth factors, clotting factors, local anesthetics, steroids, vitamins, minerals, antimicrobials, or in milder wounds antiseptics and bacteriostats.

Delivery systems of the present disclosure can deliver sleep-/relaxation-aiding actives both into the bloodstream through release into the skin, and into the brain through the trigeminal neural pathway via nasal inhalation. Many compounds and oils from nature that induce relaxation often have analgesic action as well. Thus, due to action by these substances at one or more opioid receptors, embodiments of the disclosure can be applied to release these actives and—potentially with combined transdermal and trigeminal (inhalation) delivery routes—achieve a synergistic combination of anxiolytic and analgesic actions. One embodiment that can include a combination of two actives is the combination of lavender and Melissa essential oils. Plant essential oils that are purported analgesics include lavender, wintergreen, Roman chamomile, marjoram, peppermint, rosemary, thyme, vetiver, helichrysum, ginger, lemongrass, copaiba (copal), and balsam fir. Specific fractions or components of these oils, such as menthol, can be used as well, particularly if they have substantial volatility.

The present disclosure provides drug-eluting yarns, yarn precursors, threads, filaments, fibers, and substrates that allow for ready integration into or use with existing commercial textile practices and materials. Highly desirable drug-delivery features such as near-zero-order release kinetics, high loading of active (e.g., drug), stabilization of active, and compatibility with various types of actives are also achieved. The embodiments disclosed herein may be used for improving the health of skin via local delivery of dermatological actives, but are also capable of transdermal delivery of skin-permeable actives and numerous other applications.

EXAMPLES

The following examples illustrate the present invention but are not to be construed as limiting the invention.

Example 1

The purpose of this first experiment was to determine if a coating could be found that would wet the surface of the silicone used to form the polymeric or elastomeric matrix in some embodiments and examples herein. Specifically, a Room Temperature Vulcanizing (RTV) silicone polymer sold as Novagard 200-260 was selected for imbibition because of its low viscosity (approximately 400 centipoise), which allowed for both simple processing and good imbibition uptake. Novagard 200-260 is 100% silicone and begins cross-linking upon contact with air; the skin-over time is listed as 35 minutes.

Silicone is, in the liquid state, a fluid that wets and spreads over just about any other solid material. This can be favorable for imbibition into/onto an existing yarn or other substrate material.

However, for essentially the same reasons, cross-linked silicone is a very low surface energy material that can be extremely difficult to coat uniformly—coatings tend to "bead up" like rain on a freshly-waxed windshield. Simply phrased, silicones are typically spread on other materials, and other materials do not typically spread on silicone. For example, those who work with paints generally consider silicone to be an "unpaintable" material.

Therefore, a wide range of commercially available coatings, both sprays and brush-ons, were tested for their ability to spread atop cured Novagard 200-260. Films of the RTV were poured onto a piece of cardboard and allowed to cure, after which the various coatings were applied as per instructions and normal usage. A 10×-magnification eye loop was used to examine the coatings, most of which were readily seen to be beaded up and not continuous. The non-viable coatings included cyanoacrylate ("super glue"), epoxy, natural rubber, acrylated silicone, various acrylics, and a number of adhesives that did not provide the chemical composition.

Two coatings were found to provide a continuous, smooth coating:

1. A zinc-based spray-applied coating marketed by Clearco Corp., under the product name "High Performance Zinc Spray"; the spray forms a coating that is over 90% zinc oxide; and 2. Vinyl coatings from several manufacturers, including Rust-Oleum® Specialty Vinyl Spray, which is the vinyl coating used in some other Examples below.

Both types of coatings surprisingly spread on the Novagard 200-260 silicone so as to coat the silicone surface uniformly and continuously when applied as sprays. With the vinyl coating, a uniform coating was also achieved when sprayed into a container and then applied as a brush-on liquid.

Example 2

Usnic acid is a naturally derived compound (from lichens) that functions as an analgesic, antiviral, antimitotic, and anti-inflammatory active, and has been used for its apparent activity in helping people lose weight. This active, obtained as a fine powder, was suspended at a loading of 2% by weight (20 mg/gm) in a sample of Novagard 200-260 RTV silicone polymer. Usnic acid is a good active for release experiments because it is strongly absorbing at wavelengths around 300 nanometers, in addition to being very useful for personal health.

The suspension of usnic acid in Novagard 200-260 was then imbibed into and/or onto 30-weight cotton thread (mercerized, 100% cotton), by passing the cotton through the usnic-in-RTV suspension over a length of about 10 inches. Weighing identical lengths before and after imbibition showed that the thread doubled in weight, i.e., that the increase in weight per unit length was about 100%, or $\beta$=1.0.

It was found that if yarn segments contact each other during the process of curing (cross-linking), then they become difficult to separate, making retrieval of usable yarn a very difficult process. So a special apparatus was designed that collected the freshly imbibed yarn in such a way that it isolated each segment of yarn from the rest of the yarn and from any other material, except for small (approximately 0.5 inch) contact points every 9 inches. At these contact points, the imbibed yarn was resting against a screw-threaded steel rod, six of which were aligned vertically in a hexagon arrangement of diameter 18 inches, and the cured yarn did not stick strongly to the metal. Briefly, as a carousel containing these six 3-foot-long rods was spun by a motor drive, the freshly imbibed yarn was directed into the screw-threads (13 per inch) on the steel rods, dropping down one screw-thread per carousel revolution. This ensured that approximately 95% of the imbibed yarn was free from contact with anything except air during the time that the imbibed fluid was drying and/or curing.

After curing at room temperature for 24 hours, a zinc oxide based coating was applied from a spray can to the imbibed and cured thread. The coating used was the "High Performance Zinc Spray" described in Example 1. Some of the imbibed yarn was intermittently coated, as per certain embodiments of the present disclosure. Other portions of the imbibed yarn were fully coated, having 0% open area for testing the coating properties. A fully coated, as opposed to intermittently coated, yarn should exhibit minimal release at the appropriate timescale. This was tested in the next example.

Example 3

The fully coated yarn of Example 2 was tested for the occlusiveness of the coating, using conditions that are extreme for a coating. The yarn was placed in an organic solvent, 1-pentanol, that not only solubilizes (dissolves) the active usnic acid, but does so very quickly due to low solvent viscosity and MW, and also tends to swell or even solubilize just about any material it comes into contact with.

Portions of yarn from Example 2, of uncrimped length 44 centimeters, and with various coating extents, were immersed in 20 milliliters of 1-pentanol, and samples at 0, 30, 120 minutes and 24 hours were analyzed for absorbance at 290 nanometers, near the major absorbance peak of usnic acid. Five samples were analyzed, and it should be noted that the variability of active loading along the yarn was very high, as this is a sensitive parameter to control in the embodiments described herein:

Sample A: a "primer" coating applied at 100%;
Sample B: uncoated control #1;
Sample C: Clearco Zinc/binder-based spray applied at 100%;
Sample D: uncoated control #2;
Sample E: un-imbibed control, no active.

Table 1 shows the absorbance, in milli-Absorbance units, at the 30- and 120-minute and 24-hour time points:

TABLE 1

| ID | Description | 30 min | 120 min | 24 hours |
|---|---|---|---|---|
| A | 100% primer | 18 | 60 | 74 |
| B | uncoated | 18 | 35 | 69 |
| C | 100% zinc oxide coat | 2 | 0 | 17 |
| D | uncoated | 8 | 46 | 47 |
| E | control, no active | 0 | 9 | 21 |

The data in Table 1 show, first of all, that the zinc oxide coated sample released far less than uncoated or "primer-coated" yarn of the same structure before coating.

A more detailed analysis may be justified. The data indicate that something other than usnic acid was solubilized from the matrix and contributed to the absorbance. Sample E suggests that the absorbance at 24 hours had a non-usnic contribution of approximately 20 milli-Absorbance units. With this approximation, Sample C was seen to be non-releasing, in this experiment. This is in sharp contrast with the ineffective coating of Sample A, which had absorbances comparable to the uncoated controls.

The availability of coatings such as the Clearco Zinc-based coating that have the ability to strongly inhibit—if not reduce to negligible levels—the release of active from a cross-linked silicone is a surprising result particularly for those who subscribe to the prevalent notion that silicone is an "uncoatable" or "unpaintable" material.

This Example also demonstrates that coatings exist which are able to occlude an active-loaded, silicone-imbibed yarn against active release, at 100% coating.

Example 4

An 80 milligram piece of cotton thread imbibed with the same usnic acid/Novagard 200-260 suspension described above was cut into two 40 milligram pieces. One of the pieces was then fully coated (100%, with 0% open) with a coating by Valspar called "Rustoleum Vinyl." Absorbances at 290 nanometers were taken after 22 hours of immersion in 20 milliliters of pentanol. The absorbances were as follows (a 10-fold dilution was used to keep the absorbance in the range of the instrument, and then factored back in for the final result): Uncoated: 6.780; Coated (with Vinyl Rustoleum): 2.230.

Thus, this Example also showed strong retention of active even when the entire thread is immersed in a solvent liquid (pentanol).

Example 5

This Example demonstrated zero-order release using a partly but dominantly coated silicone core loaded with usnic acid as active. Samples were prepared by taking a fine, hollow tube of nylon, and loading it with a suspension of usnic acid in a silicone RTV known as "Silicone Ultra," made by White Lightning, which is 100% silicone.

Sample "A": 0.117 grams usnic acid+0.953 grams Silicone Ultra, all of which was loaded into the nylon tubing.

Sample "B": 0.101 grams usnic+1.023 grams Silicone Ultra, 0.593 grams of which was loaded into the tubing.

While approximately 99% of the usnic/silicone was surrounded by (i.e., coated by) the nylon tubing, after curing approximately 1% of the usnic/silicone protruded out of the tubing and was thus uncoated. The uncoated end of each sample was then immersed in 100 milliliters of a solvent mix with the following composition: 56.1% acetonitrile (ACN), 17.5% water, 14.2% tert-butyl acetate, and 12.2% tetrahydrofuran (THF). The two solutions were then analyzed periodically over the next 2 months for absorbance at 310 nanometers, which is determined almost entirely by the concentration of usnic acid in the solvent mix. The solvent mix was stirred gently before each sampling.

Figure 4:
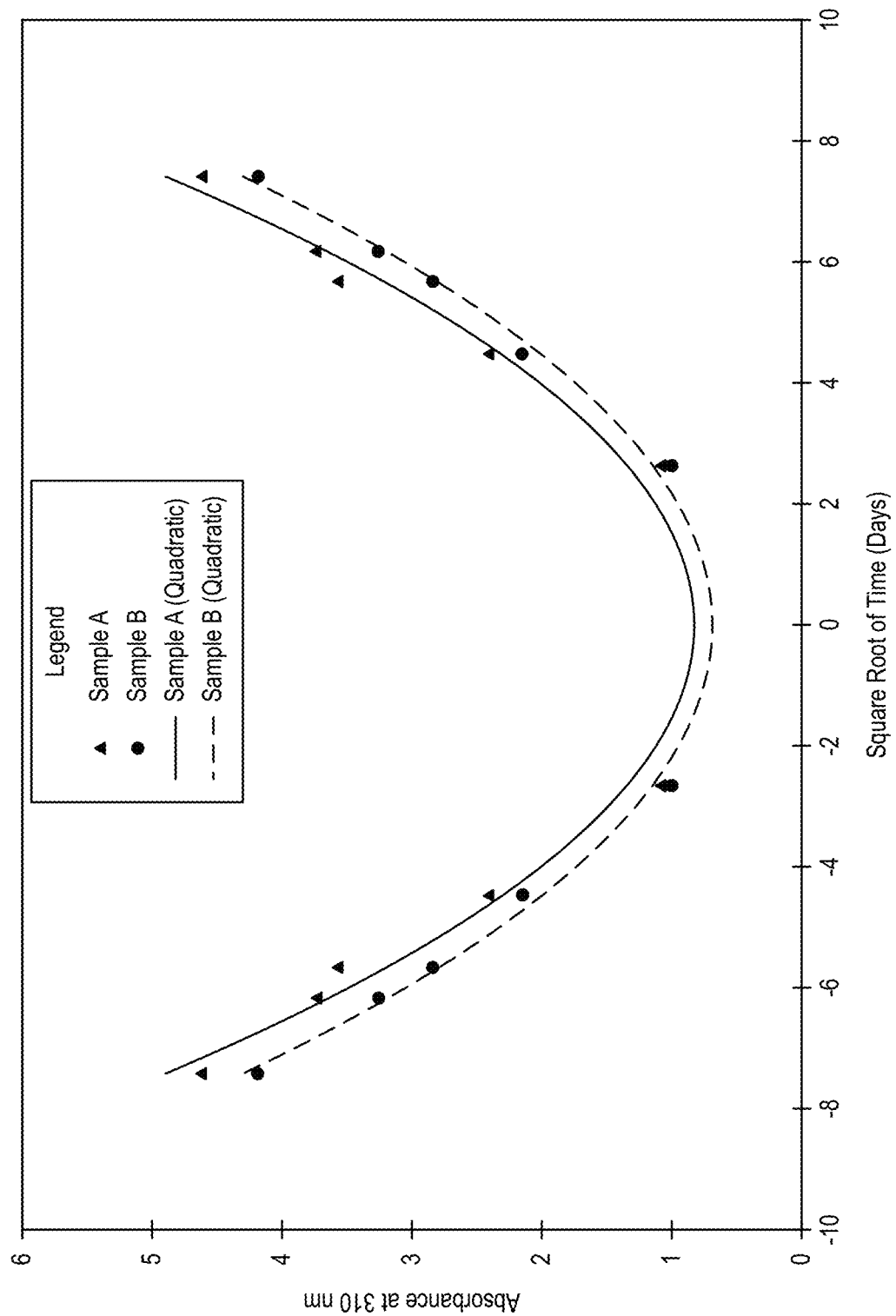
FIG. 4 is a graph of UV absorbance versus the square root of time in days for certain samples of active compounds, according to an embodiment of the present disclosure.

FIG. 4 shows the UV-absorbances at 310 nanometers plotted against the square root of time in days, for both Samples A and B. Diffusion-limited processes yield a cumulative release curve that varies as the square root of time. If that were the case here, the plots in FIG. 4 would be straight lines. However, if a best-fit linear fit is performed on the data, the Y-intercept—which is the concentration at time zero calculated using the linear fit—is strongly negative, namely −0.801. Not only is this not possible and far outside the precision of this experiment, but also the quadratic fits shown fit the two data sets (reflected across the Y-axis so as to force a purely quadratic fit, with no linear term) to very high regression coefficients, namely R=0.980 and 0.994. In addition, the Y-intercept (time zero) is positive, and in fact the value of 0.5 is in agreement with background absorbances in similar experiments. A quadratic fit, when plotting the absorbance against the square root of time, means that the absorbance varies linearly with time. And since the concentration is related to the absorbance by a constant (the molar absorptivity), this example shows that zero-order release kinetics—where the cumulative amount of active released is proportional to the time, making the release rate a constant—is indeed observed with the partly but dominantly coated architecture.

Another similar sample, but with a (soft-segment) polyurethane as an polymeric or elastomeric matrix material, and a concentration of usnic acid that is only half the above case, showed a release rate that was approximately the same as that of this silicone-based material.

Example 6

Using the imbibition and collection apparatus described in Example 3, yarns as per embodiments of the present disclosure were prepared using several chemistries. In each case at least 100 yards, and in most cases over 300 yards, were produced. The chemistries are summarized in Table 2. In each case, the active was loaded to a level of 1% in a polymeric or elastomeric matrix. The "zinc oxide" coating in Table 2 refers to the "High Performance Zinc Spray" from Clearco discussed above.

TABLE 2

(*Kraton IR401)

| Active compound | Polymeric matrix | Coating | Substrate yarn |
|---|---|---|---|
| Hydrocortisone | Polyisoprene emulsion* | Zinc oxide | 1/150/34 polyester |
| Usnic acid | Novagard 200-260 | Rustoleum Vinyl | 30-wt cotton |
| Pyrithione zinc | Novagard 200-260 | Rustoleum Vinyl | 1/150/34 polyester |
| Retinoic acid | Novagard 200-260 | Zinc oxide | 1/150/34 polyester |
| CoEnzyme Q10 | Novagard 200-260 | Zinc oxide | 30-wt cotton |
| Curcumin | Polyisoprene emulsion* | Zinc oxide | 1/150/34 polyester |
| Curcumin | Novagard 200-260 | Zinc oxide | 1/150/34 polyester |
| Arecoline | Novagard 200-260 | Zinc oxide | 1/150/34 polyester |

In order to cross-link the polyisoprene in the two cases above (first and sixth rows), the yarn was placed in an oven at 300° F. for one hour.

Example 7

An uncoated, imbibed yarn, with polyester substrate yarn imbibed with a 10% by weight suspension of arecoline hydrobromide in Novagard 200-260, was woven into a small piece of fabric made 100% from that yarn. This was then tested in a Franz cell apparatus (Zyleris Pharmatech) for its ability to deliver the active (arecoline) transdermally. Another portion of the imbibed yarn was intermittently coated as per an embodiment of the disclosure (see the last row of Table 2), but for demonstrating transdermal delivery it was reasoned that uncoated was best.

One skilled in the art will be familiar with the design of a Franz cell. The test article, in this case the aforementioned arecoline-loaded fabric, was placed atop a small piece of freshly excised skin, in this case from a pig's ear; below the skin was a reservoir containing bovine serum albumin buffer to simulate blood plasma. In order to reach the reservoir, the active had to diffuse transdermally across the layer of skin. Three such Franz cells were used so that the experiment was done in triplicate. A small aliquot was drawn from each reservoir at the 24-hour point and tested for arecoline as now described.

Figure 5:
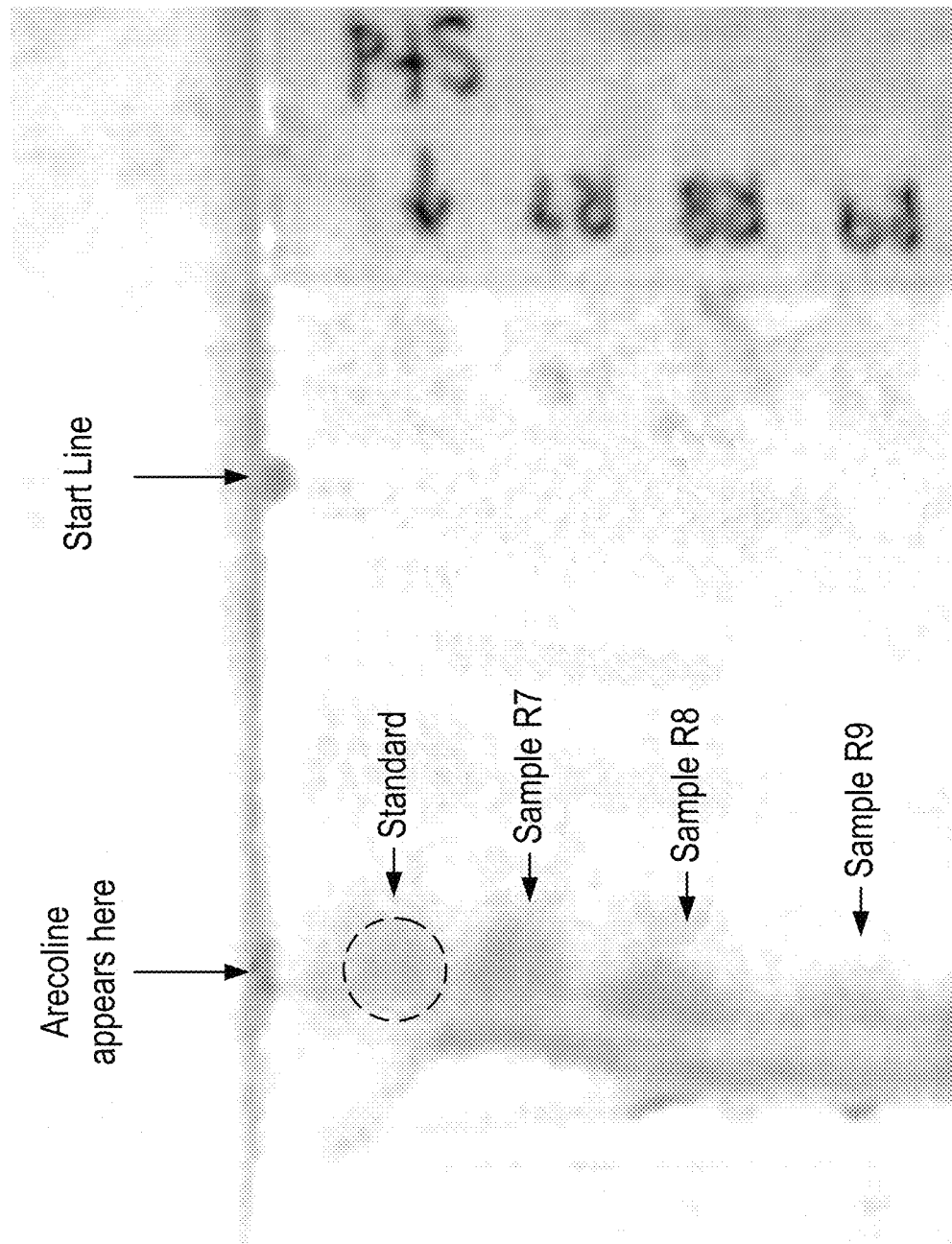
FIG. 5 is a photograph of a thin layer chromatography plate spotted with samples of active compounds, according to an embodiment of the present disclosure.

A reference arecoline solution was prepared by dissolving approximately 3 milligrams arecoline hydrobromide (ScienceLab.com) in approximately 0.5 milliliters of bovine serum albumin buffer, for an approximate concentration of about 6 milligrams/milliliter. The reference solution was spotted alongside all three samples (labelled R7, R8 and R9) on a TLC plate at the origin. After driving out the water from the spots with heat, the spotted TLC plate was allowed to cool, then developed in 100% methanol inside a developing tank. After development, spots were visualized after 1) dipping the plate in 0.02 M aqueous copper nitrate solution, 2) heating on a hotplate, 3) allowing it to cool, 4) dipping in 0.05 M aqueous potassium iodide and 5) heating on a hotplate. The reference solution yielded a faint brown spot running just behind the solvent front. All three sample solutions yielded a brown spot of the same order of intensity as that from the 6 milligram/milliliter reference solution, and at the same retention factor as the brown spot from the reference solution. See FIG. 5 for a photograph of the resulting TLC plate.

The approximate retention factor was 0.88. Based on the observation of equal, or even greater, spot intensity for the samples as compared to the reference, the concentration of arecoline in the reservoirs was on the order of 5 milligrams/milliliters. Thus, the imbibed yarn is effective at transdermal delivery of arecoline, according to this standardized pig ear skin Franz cell model.

Example 8

Figure 6:
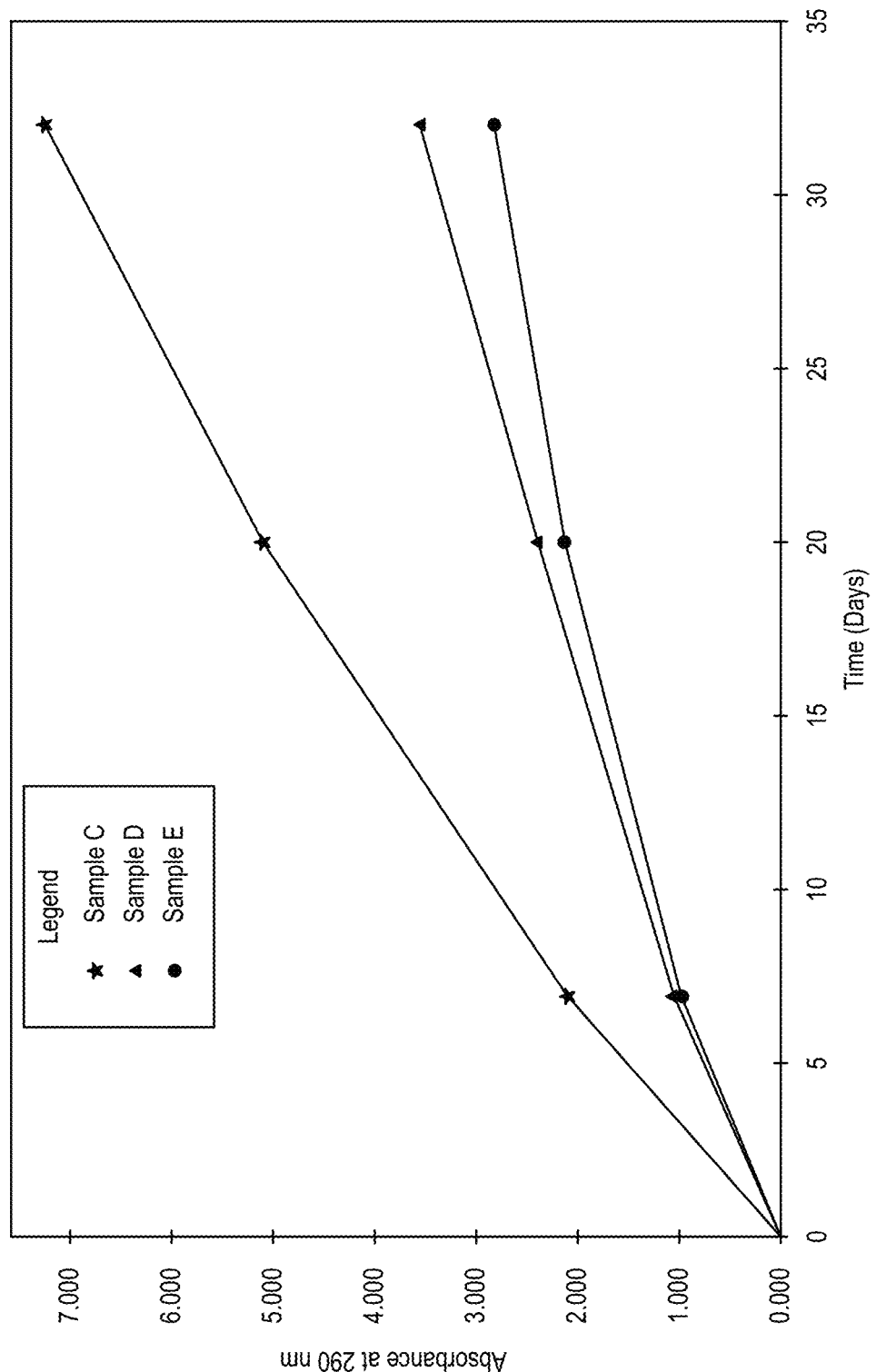
FIG. 6 is a graph of UV absorbance data showing the near-zero order release of an active compound, usnic acid, according to an embodiment of the present disclosure.
Figure 7:
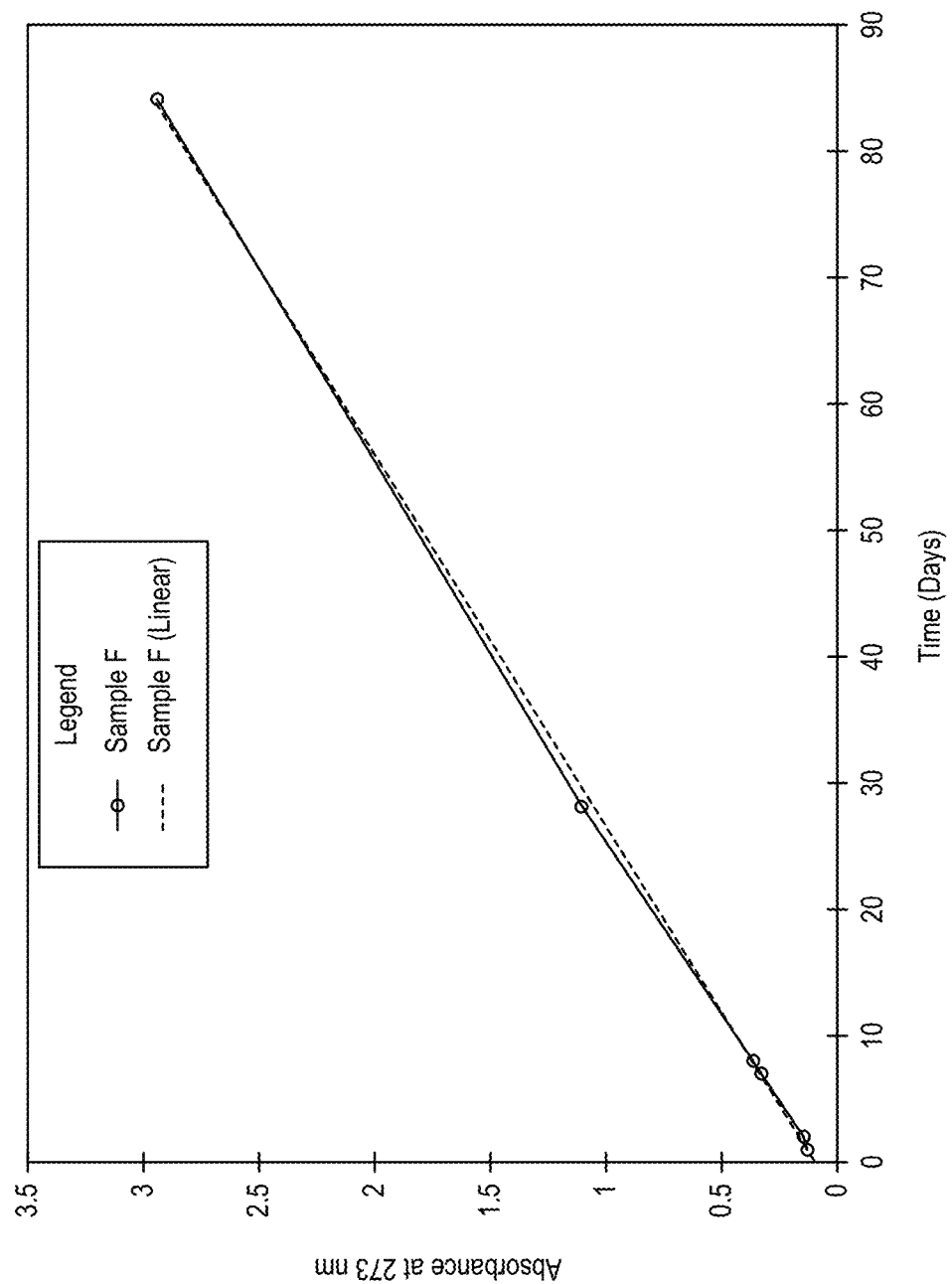
FIG. 7 is a graph of UV absorbance data showing the near-zero order release of an active compound, terbinafine hydrochloride, according to an embodiment of the present disclosure.
Figure 8:
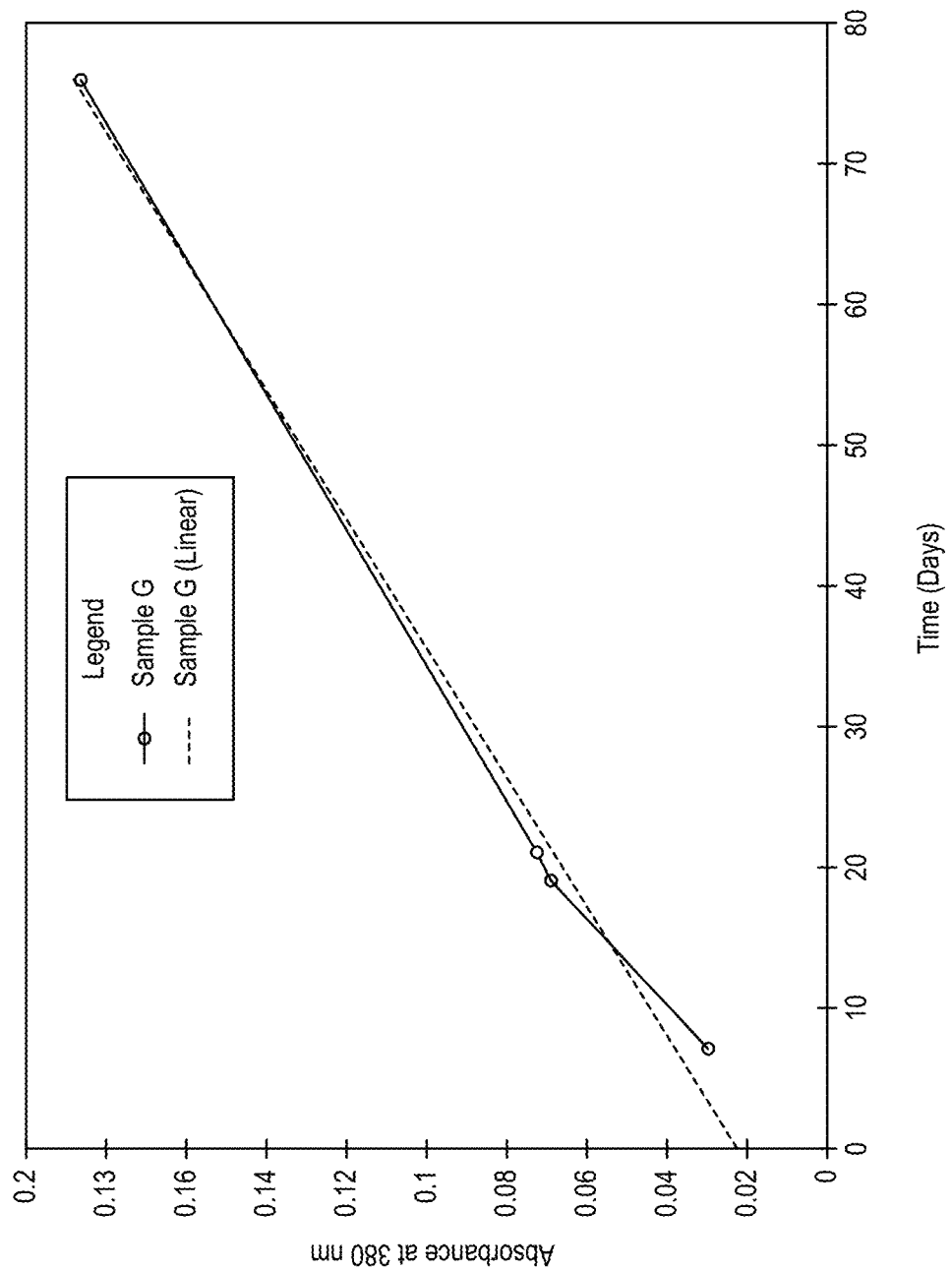
FIG. 8 is a graph of visible light absorbance data showing the near-zero order release of an active compound, dantrolene, according to an embodiment of the present disclosure.

Exemplary drug release profiles according to embodiments of the present disclosure are depicted in FIGS. 6-8. These drug-release profiles were measured from intermittently coated yarns and are consistent with near-zero order release kinetics.

Referring first to FIG. 6, these results were obtained from UV-Vis spectroscopy and represent the release of the naturally occurring antifungal and antimicrobial compound usnic acid. Samples C-E each contained one yard of 30-weight cotton yarn imbibed with a matrix polymer containing dispersed usnic acid. After curing the matrix polymer, each of Samples C-E were intermittently spray coated (approximately 80% coated) with an aerosol product marketed as Rustoleum Vinyl. Sample C contained a polyurethane matrix polymer (Rovene 4021), and the amount of matrix polymer incorporated onto and/or into the yarn approximately doubled the weight of the yarn, i.e., a weight increase on the order of 100%. Samples D and E each contained a polysiloxane matrix polymer (Novagard 200-260), and the amount of matrix polymer incorporated onto and/or into the yarn approximately doubled the weight of the yarn, i.e., a weight increase on the order of 100%. The samples were then placed in a pentanol solution and gently rocked, during which the release of usnic acid was measured as the absorbance at 290 nanometers, the results of which demonstrated a near-zero order release as depicted in FIG. 6.

FIG. 7 depicts near-zero order release of terbinafine hydrochloride. Sample F contained one yard of polyester yarn (150 Denier) imbibed with a matrix polymer of polyurethane (Rovene 4021) containing dispersed terbinafine hydrochloride. The amount of matrix polymer incorporated onto and/or into the yarn approximately doubled the weight of the yarn, i.e., a weight increase on the order of 100%. A polyurethane coating, marketed under the name "ZAR Exterior Polyurethane," was intermittently applied to achieve a coating on approximately 90% of the yarn. The release of terbinafine hydrochloride into water was measured as the absorbance at 273 nanometers, the results of which are depicted in FIG. 7, which also includes a linear fit of the data points.

FIG. 8 depicts the near-zero order release over 3 months of the antispasmotic drug dantrolene sodium from a one-yard portion (Sample G) of intermittently coated yarn (150 Denier polyester yarn) as per the disclosure, releasing into a weakly buffered aqueous solution at pH approximately 11.0, with absorbance measured at 380 nanometers, a known absorbance peak of aqueous dantrolene sodium. FIG. 8 also includes both the absorbance measurements and a linear fit of the data points. Novagard 200-260 RTV was used as the polymeric matrix in which the dantrolene was dispersed. The amount of matrix polymer incorporated onto and/or into the yarn approximately doubled the weight of the yarn, i.e., a weight increase on the order of 100%. The release kinetics of this strongly absorbing (and thus accurately measured) drug is very close to perfect zero-order, constant rate of release. The coating applied was a "hard" polyurethane coating supplied as an aqueous dispersion purchased from Alberdingk-Boley under the product designation "Aliphatic Polyurethane Dispersion U-933." The coating was applied by a brush-painting operation, performed by a professional artist instructed to coat 10 centimeter-wide stripes separated by unpainted (uncoated) stripes of approximately 2.5 centimeters (resulting in an approximately 80% coated yarn); the stripes were vertical on a vertically oriented, batch-mode accumulator.

Example 9

This example demonstrates exemplary coating methods according to embodiments of the present disclosure. A spray-coating was conducted using a model AA10000JJAU-03 spray gun, a PFJ2050 fluid cap, and a PAJ45350-40-SS air cap (each from Spraying Systems Co.). After each segment of testing the spray tip was submerged in water and fired several times in order to keep the acrylic from hardening.

Figure 9:
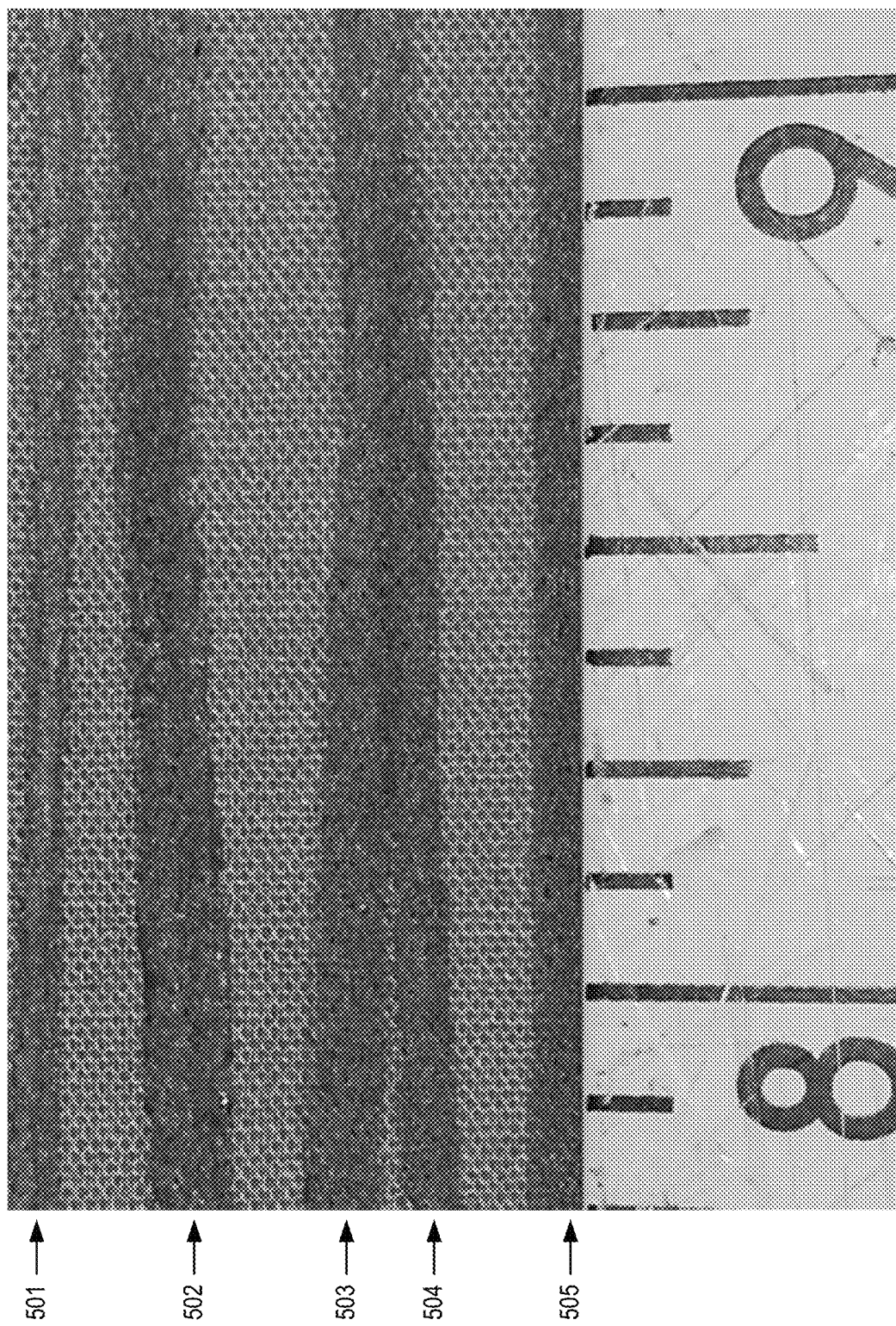
FIG. 9 is a photograph depicting a coated yarn, according to an embodiment of the present disclosure.

A bulked or textured 150 Denier yarn was first imbibed with Novagard 200-265 "fast-cure" RTV, after which the bulk and/or texture was maintained. After drying, approximately 3 yards of the imbibed yarn was wrapped around a 5-inch open frame, and the spray gun loaded with Alberdingk AC2523 self-cross-linking acrylic coating mixed with a green food coloring to aid in visualizing the coating. The loaded spray system was pulsed 15 times at 20 milliseconds per pulse, spraying at a nozzle-to-yarn distance of approximately 5 inches. This provided a rather uniform coating, and as seen in the close-up photograph in FIG. 9, the bulk or texture of the yarn was maintained—in other words, each individual fibril was coated separately. This offers many advantages over other coating processes that "glue" the fibrils together resulting in a "flat" yarn, such as increased comfort, circumvention of the need to ply the yarn, increased surface area of skin contact, and compatibility with standard yarn and textile processes. As is also seen in FIG. 9, a ruler was placed alongside yarn samples (501, 502, 503, 504, 505) to demonstrate that the bulk or texture was maintained, since a flat yarn of this Denier would be less than 1/64th of an inch in width, whereas this yarn's bulk or texture provided an expanded width that was over 1/16th of an inch. In another similar coating method, 1.5-inch wide strips of a soft foam were glued to a drum 7 inches in diameter, leaving 1/4-inch gaps between them.

Example 10

Experience with water-borne coatings, such as Alberdingk acrylic dispersion "AC 2523," indicated that texture can be difficult to maintain upon coating a bulked or textured yarn with a formulation that contains 20% or more water, whether the yarn had been imbibed with RTV or not. Even when tension on the yarn was kept below 10 grams, bulk or texture was lost after the coating had dried/cured, resulting in a "flat" yarn. This Example used a water-free, solvent-free coating to test whether bulk or texture could be maintained.

Figure 10:
FIG. 10 is a photograph depicting a coated yarn, according to another embodiment of the present disclosure.

A cyanoacrylate adhesive, Gorilla superglue, was applied to coat a yarn which had previously been imbibed with a dispersion of aspirin powder (25% by weight) in Novagard 200-265 ultralow viscosity RTV. The imbibed and cured yarn, still bulked and texturized, and of measured Denier of approximately 90 D, was then passed through a small container of Gorilla superglue, with the residence length being approximately 2 millimeters and the residence time on the order of 10 milliseconds. Tension in the line was not measured but was high, well in excess of 10 grams. The Denier increased to over 300 D, as the yarn picked up a very large amount of superglue. Nevertheless, the final yarn, after the superglue had cured, was still bulked or texturized. FIG. 10 shows a photograph of the final yarn 506 of the invention after imbibition with RTV/aspirin and subsequent coating with the cyanoacrylate. While the photograph does not capture all of the detailed structure, the bulk and texture are evident.

Example 11

This example provides an exemplary method for large-scale yarn production. Tests in the inventors' lab have demonstrated the feasibility of each step discussed here, and one skilled in the art will understand the methods described. Bulked or textured yarn coming off a creel will first pass through a reservoir of RTV or other matrix source, which has a low enough viscosity that it is imbibed into the yarn, which is perhaps more accurately described as covering each fibril; if the viscosity is too high, then the Deborah number of the imbibition may be too high to provide a contiguous film of matrix. At a typical yarn speed on the order of 10 meters per second, the yarn passes through a chamber or sack containing a thickness of matrix on the order of ¼ inch, making a residence time of ¼ inch/10 meters/second or roughly 1 millisecond. At least in the case of a silicone-based matrix, results have consistently shown that this is sufficient time to leave a contiguous film of silicone on each fibril of the yarn (for textured polyester and nylon yarns), and the Denier increases by approximately 50%. For cases where a larger loading of active is required, the residence time can be increased to several milliseconds. However, if the Denier increases by more than 100% (i.e., more than doubles in weight per unit length), there is increasing risk that the yarn will go flat and lose texture, which is generally undesirable. It may be advantageous to maintain an inert, dry atmosphere at the chamber to limit or eliminate any premature curing of the RTV.

After passing through the chamber and imbibing the RTV (or other matrix source), the RTV should be substantially cured before moving on to the coating stage, otherwise the low surface energy of the matrix can promote migration of the wet RTV over the intended coating. Strong ultraviolet light can cure some RTVs (such as Novagard 200-260) in a few seconds, though this presents some costs and exposure hazards. Warm, humid air can be used to trigger or initiate the cross-linking reaction, which in the case of Novagard 200-265 is substantially complete in 3 to 5 minutes. A single-end or multiple-end slasher is then used to temporarily wind the imbibed, drying yarn, moving it along slowly such that during the 3 to 5 minute curing time, only a small fraction (less than 10%) of the drying yarn contacts any solid and yarn-yarn contacts are avoided. At a production speed of about 10 meters per second, the slasher needs to hold about 2,500 yards of yarn per end in order to provide adequate drying time before moving on to the next step which involves contacting a solid. Yarns should be spaced approximately ¹/₁₆ inch apart, and a multi-end slasher may be desirable, particularly since most commercial slashers space the yarns at considerably higher spacings than ¹/₁₆ inch, leaving ample space for multiple yarn ends while still avoiding or at least minimizing contact between adjacent winds.

Coming off the slasher, the now substantially dried yarn passes around a drum which is rotating slightly faster than a second drum on the exit side of the coating chamber; this "relaxes" the yarn so that in the coating process, the fibrils making up the yarn are "bulked," or substantially separated from each other in a more open configuration. Other methods, such as invoking accumulators, are known in the art for relaxing yarn during continuous-mode production steps. The imbibition step is generally quite forgiving of tension—flattening from over-applying the RTV rather than from tension—and so it is generally not a problem if the faster-rotating drum is controlling the speed of passage through the imbibition chamber.

After passing around the first (faster-spinning) drum, the yarn enters the coating chamber which, depending on the plant/worker conditions and details of the coating chemistry, might benefit from an enclosure, with very small openings for the entry and exit of the yarn. The (now-relaxed) yarn then passes in front of an array of spray nozzles, e.g., two nozzles for the "left" and "right" sides of the yarn. While a pulsing of the spray gun is possible, intermittency of the coating is more sharply defined if a mask is used. Thus a belt with openings cut into it is driven around a system of pulleys such that the velocity of the belt matches that of the yarn (about 10 meters per second) over the region where the belt comes between the nozzle and the yarn (meaning that two belts may be necessary for a two-nozzle system). Between the openings in the belt/mask are solid regions blocking or diverting the spray so as to leave uncoated segments on the yarn of the desired length; in general these will constitute on the order of 10% of the yarn, since 90% will be coated, so that the wasting of this "blocked" fraction of the spray is small. Alternatively, this mask can be timed with a pulsing of the spray, eliminating most of the wastage due to blocking while still allowing for a crisp, well-defined intermittent pattern on the yarn.

Multiple ends entering the coating chamber provide not only a higher production rate, but also more efficient use of coating (which may be difficult or expensive to recirculate). Spray nozzles capable of restricting the spray to ¹/₁₆ inch width are difficult to come by, so if, say, 12 yarns are spaced ¹/₁₆ inch apart at the point of coating application, this three-fourths inch is much closer to the typical width of a spray pattern.

After passing from the coating chamber (and enclosure, if present), the yarn may need to be stored on a second slasher, if the coating takes minutes to dry. However, tests with the acrylic coating Alberdingk AC 2523, for example, have shown that yarn can be wound onto a cone directly from the coating chamber, skipping any slasher or accumulator, provided that the Denier of the yarn is below about 200 (yarn thicker than this is more prone to sticking to itself), particularly if a few tens of feet are traversed by the yarn between the coating and the cone. Drying methods, as simple as blowing air onto the yarn, can be applied during the traversal of this distance.

Many post-processing steps can then be applied as needed. If conditions are such that the yarn can benefit from plying with one or more other yarns, then plying can be used to alter the "hand," color, elongation, or processibility, or to combine properties of two or more yarns.

Example 12

This Example provides exemplary release tests on fabrics from yarns of the disclosure. These release measurements were performed on small swatches of fabric produced from yarn of the disclosure, and washed or otherwise stressed before release testing. Release was used to quantify how much active is retained intact after the stress. No coating was necessary for this test. Retention of active through stresses such as washes and scouring is a key distinguishing benefit of yarns of this disclosure and enables medicated fabrics that can be applied in a wide range of applications that demand washability in order to be commercially viable.

Aspirin (acetylsalicylic acid) was ground to a fine powder and dispersed at 25% wt/wt in Novagard 200-260. This was imbibed into a texturized 70 Denier nylon yarn, then plied with a textured 70 Denier nylon yarn. The yarn was then knitted into several sleeves. In an informal test, wearing a sleeve was sufficient to provide significant analgesia when worn on the elbow or knee.

Washing with hot detergent water was then done once (on swatch #2), 5 times (swatch #3), or 10 times (swatch #4). Swatch #1 was the control with zero washings. Each swatch, a fixed 1-inch square, was placed in water for release, and after two days the absorbance measured at 280 nanometers.

TABLE 3

|  | Control (0 washes) | 1 wash | 5 washes | 10 washes | Dyed |
|---|---|---|---|---|---|
| Absorbance (at 280 nm) | 0.097 | 0.077 | 0.038 | 0.045 | 0.051 |

These data show retention of about 45% of the active after 10 washings.

Another sleeve was dyed using a standard dyeing process, which included scouring at the upper limit of the normal range of temperatures in dyeing, namely 220° F. for 45 minutes. This result is shown in the last column of the above table. Over 50% potency was retained through this intense process.

Example 13

Allantoin, which is frequently used as an active in skin creams, was dispersed in RTV at 25%, and this matrix imbibed into a 40 Denier texturized nylon yarn. Some of this was plied with a 40 Denier nylon yarn. Another portion was air-covered with a spandex yarn. Testing revealed a skin-soothing, softening effect when used, due at least in part to a moisturizing effect.

Example 14

Other actives were incorporated into or onto yarns in accordance with the present disclosure, including caffeine, ibuprofen, acetaminophen, cetyl palmitate, capsaicin, and menthol. In each instance, the active was successfully incorporated into or onto a yarn substrate with a polymer matrix.

Example 15

Figure 11:
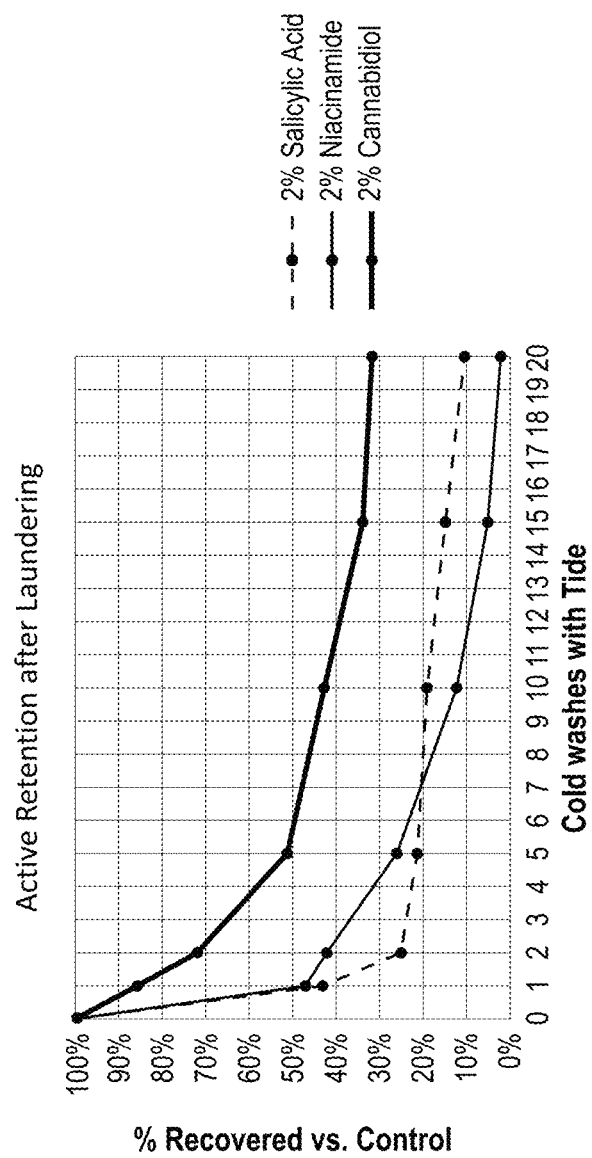
FIG. 11 is a graph showing active retention after laundering.

90-meter coated yarn samples were laundered for approximately 40 minutes with a cold wash using TIDE® detergent. Yarn samples were removed at various points, air-dried, and remaining active was extracted with a solvent. The resulting extract was analyzed by HPLC to determine the total active present in the yarn. This was plotted as a percentage of the active extracted from an unwashed control sample (see FIG. 11).

Example 16

Figure 12:
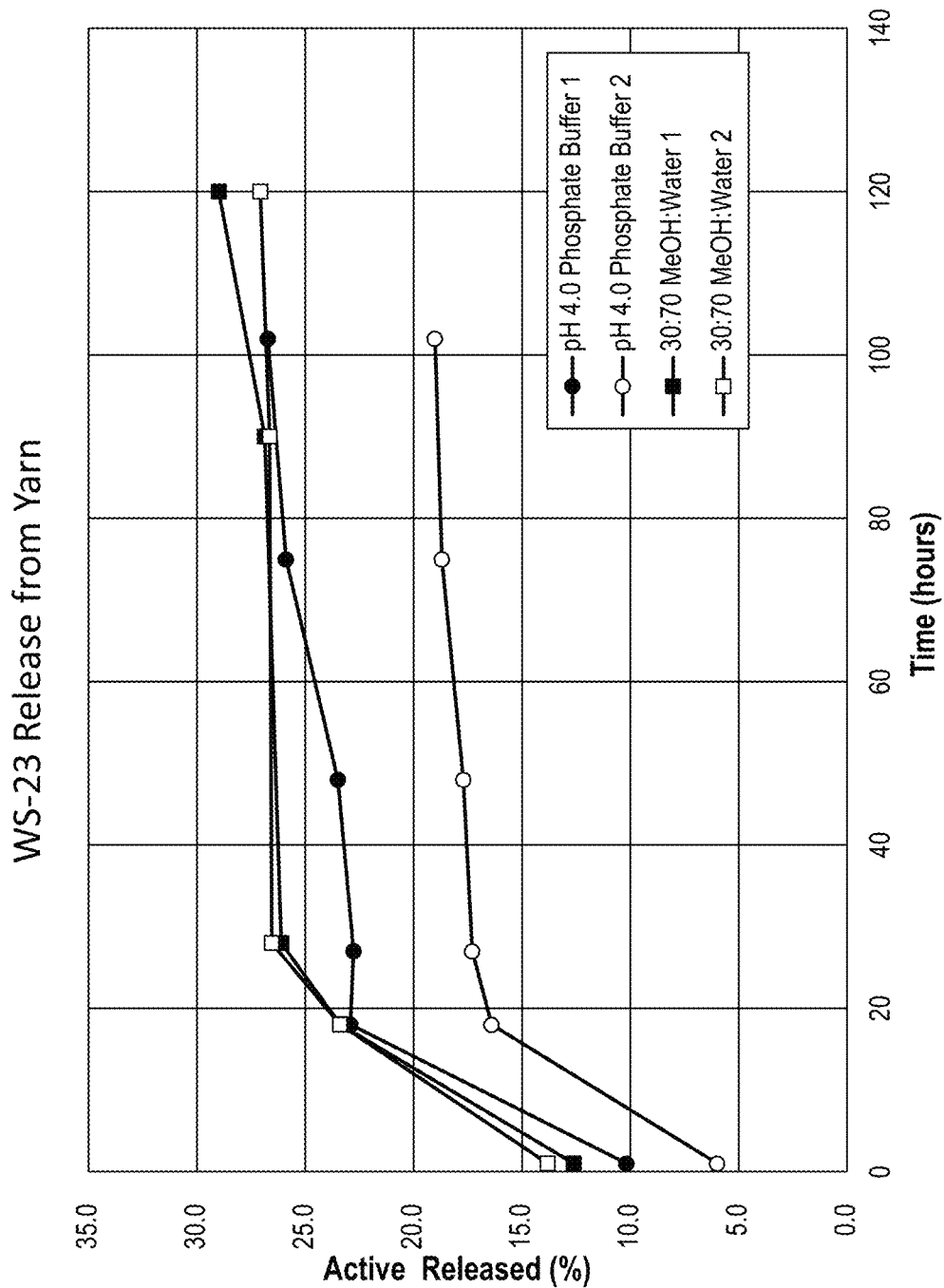
FIG. 12 is a graph showing WS-23 release from yarn.

90-meter coated yarn samples containing 15% 2-isopropyl-N,2,3-trimethylbutyramide (WS-23) were submerged in two different solvent systems to release active. Solvent was sampled periodically and analyzed by gas chromatography (GC). Release was plotted as a percentage of total active present in yarn (see FIG. 12).

Example 17

Figure 13:
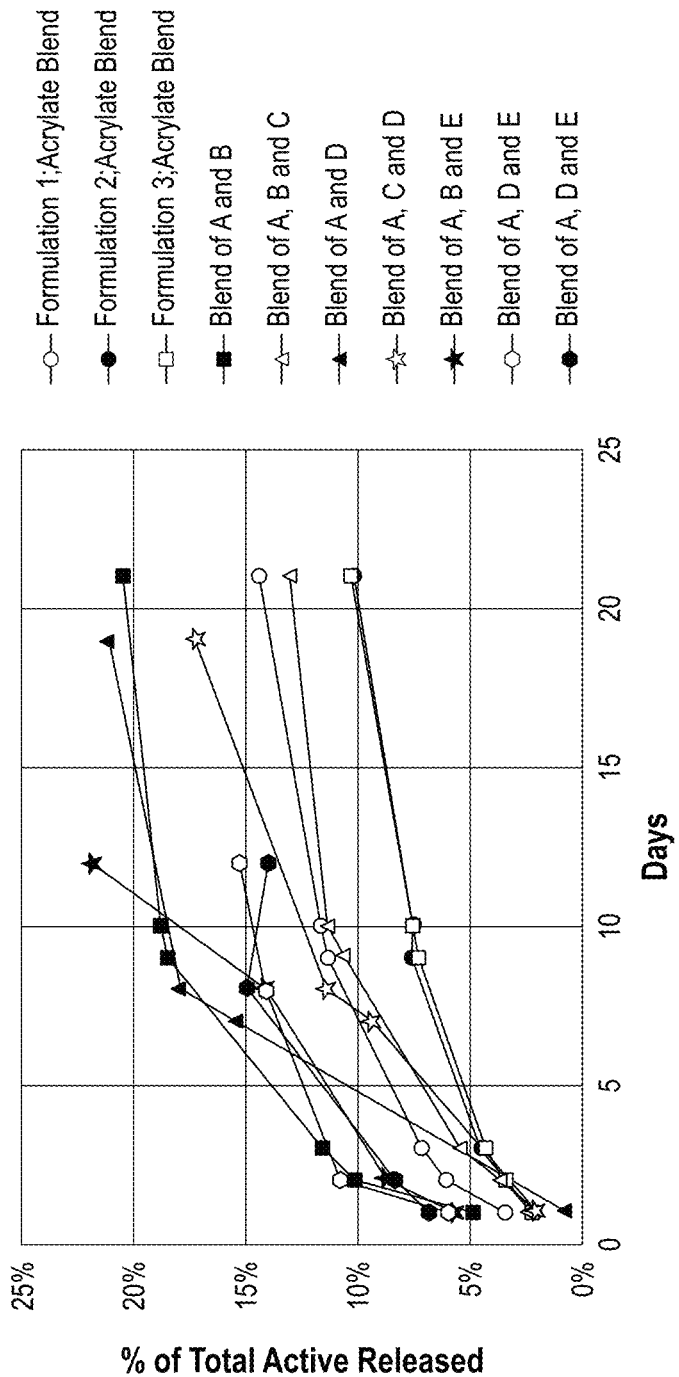
FIG. 13 is a graph showing nonivamide release from various polymeric coatings.

Various coating formulations were loaded with 5% nonivamide. 2.0 gram disks of each coating were cured by UV under $N_2$. These samples were then submerged in 100 mL of a 30:70 MeOH: water solvent system. This solution was sampled over a period of up to 21 days with volume replacement after each sampling. Solutions were analyzed by HPLC and plotted as a percentage of total nonivamide present in each sample (see FIG. 13).

Example 18

Figure 14:
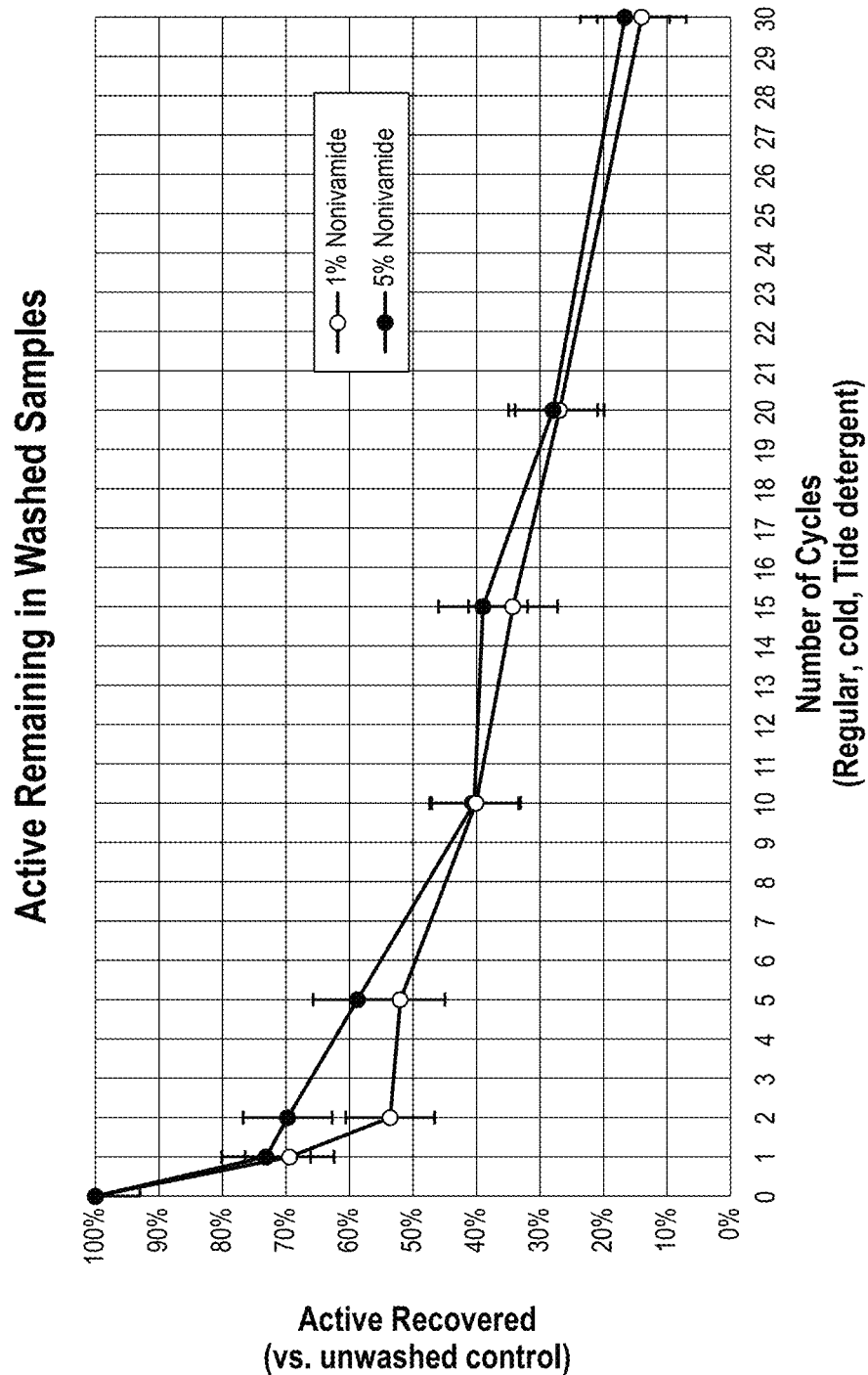
FIG. 14 is a graph showing active remaining in washed samples.

Samples were produced at two different active loadings (1% and 5% nonivamide. Samples were then washed 1, 2, 5, 15, 20 and 30 times in cold water, with one TIDE® detergent pod, using a regular wash setting (about 40 minutes). Active remaining was quantified and plotted with respect to an unwashed control sample (see FIG. 14).

Example 19

Figure 15:
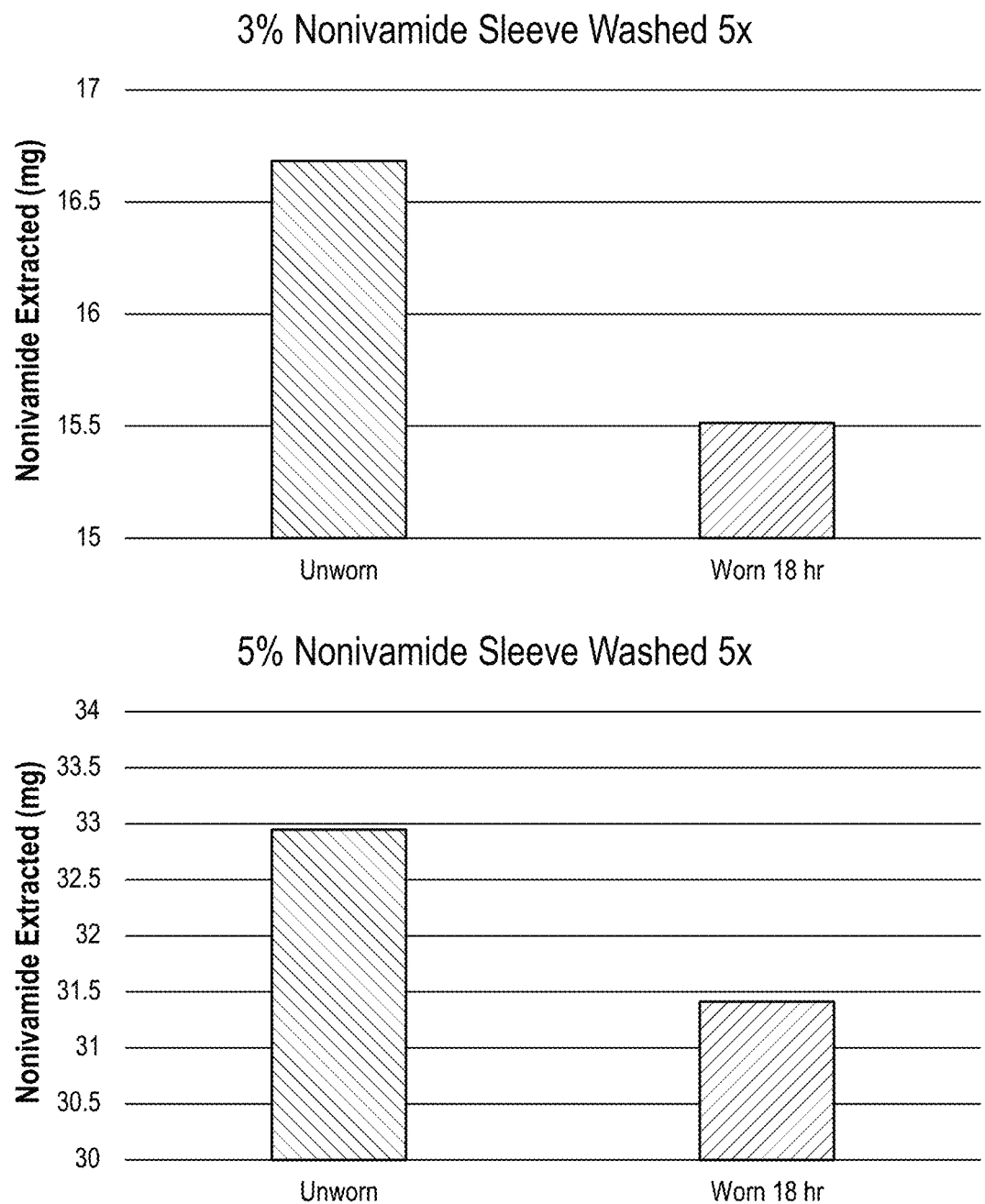
FIG. 15 is a series of graphs showing extraction of nonivamide from sleeves loaded with 3% and 5% nonivamide, respectively.

Sleeves made from activated yarn, prepared as disclosed herein, were washed multiple times and worn for extended periods. Solvent extraction determined the mass of nonivamide remaining in the garment and the average rate of nonivamide release over the duration of the wear (see FIG. 15). It was found that after several washes, the sleeves released within the effective dose range, and retained enough active for an additional 25-35 doses. Based on a typical topical cream, the effective daily dose of capsaicin for relief in the foot, ankle, and calf range from 0.5 to 6 mg depending on the severity of pain. Experimental results generated by wear testing has shown that after multiple washings, the activated yarn still released active comfortably within this range (1.8 to 2.4 mg). While the majority of active losses are incurred during wash cycles, it has been determined that after 30 washes, a sock made from activated yarn may retain enough active for 10 or more additional doses.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. The scope of the invention is therefore defined by the following claims and their equivalents.

The invention claimed is:

1. A method for manufacturing an imbibed substrate, the method comprising:
   contacting a solution of at least one monomer, an initiator, and cannabidiol with a substrate, wherein the substrate is selected from a yarn, a yarn precursor, a thread, a filament, and a fiber; and
   exposing the solution and the substrate to UV light sufficient to initiate polymerization of the monomer.

2. The method of claim 1, wherein the solution further comprises an oligomer.

3. The method of claim 2, wherein the oligomer is an acrylate stabilizing additive.

4. The method of claim 1, wherein the solution further comprises one or more of methyl salicylate, ethyl salicylate, arnica oil, peppermint oil, menthol, lidocaine, benzocaine, capsaicin, nonivamide, niacinamide, caffeine, hydrocortisone, and derivatives thereof.

5. The method of claim 1, wherein the monomer is an alkyl methacrylate monomer selected from the group consisting of methyl methacrylate, ethyl methacrylate, n-propyl methacrylate, isopropyl methacrylate, n-butyl methacrylate, t-butyl methacrylate, sec-butyl methacrylate, pentyl methacrylate, 2-ethylhexyl methacrylate, 2-ethylbutyl methacrylate, n-octyl methacrylate, isobornyl methacrylate, isooctyl methacrylate, isononyl methacrylate, and lauryl methacrylate.

6. The method of claim 1, wherein the monomer is an alkyl acrylate monomer selected from the group consisting of methyl acrylate, ethyl acrylate, n-propyl acrylate, isopropyl acrylate, n-butyl acrylate, t-butyl acrylate, sec-butyl acrylate, pentyl acrylate, 2-ethylhexyl acrylate, 2-ethylbutyl acrylate, n-octyl acrylate, isobornyl acrylate, isooctyl acrylate, isononyl acrylate, and/or lauryl acrylate.

7. The method of claim 1, wherein the step of exposing the solution and the substrate to UV light to initiate polymerization of the solution forms a polymerized coating on the substrate, and wherein the polymerized coating has a glass transition temperature ($T_g$) selected from a range of between about −60° C. and about 110° C.

8. The method of claim 1, wherein exposing the solution and the substrate to UV light occurs in a light box comprising one or more inert gases.

9. The method of claim 8, further comprising twisting the substrate with a yarn of greater elasticity than the substrate.

10. The method of claim 2, wherein forming the solution further comprises:
    (i) mixing the monomer and the oligomer to form the solution;
    (ii) warming the monomer and the oligomer mixture between 25° C. and 50° C.;
    (iii) adding the initiator to the solution; and
    (iv) adding the cannabidiol to the solution.

11. The method of claim 1, further comprising rewinding the substrate into a bundle after the monomer has been polymerized on the substrate.

12. An imbibed substrate comprising
    a substrate comprising at least one of a yarn, a yarn precursor, a thread, a filament, and a fiber; and
    a polymer matrix comprising cannabidiol dispersed in the polymer matrix;
    wherein the polymer matrix is imbibed on at least a portion of the substrate.

13. The imbibed substrate of claim 12, wherein the polymer matrix is cross-linked.

14. The imbibed substrate of claim 13, wherein the polymer matrix is an alkyl acrylate polymer or an alkyl methacrylate polymer.

15. The imbibed substrate of claim 14, wherein the polymer matrix is an alkyl methacrylate polymer selected from poly(methyl methacrylate), poly(ethyl methacrylate), poly(n-propyl methacrylate), poly(isopropyl methacrylate), poly(n-butyl methacrylate), poly(t-butyl methacrylate), poly(sec-butyl methacrylate), poly(pentyl methacrylate), poly(2-ethylhexyl methacrylate), poly(2-ethylbutyl methacrylate), poly(n-octyl methacrylate), poly(isobornyl methacrylate), poly(isooctyl methacrylate), poly(isononyl methacrylate), poly(lauryl methacrylate), and blends or copolymers thereof.

16. The imbibed substrate of claim 13, wherein the polymer matrix is an alkyl acrylate polymer.

17. The imbibed substrate of claim 16, wherein the alkyl acrylate polymer is selected from poly(methyl acrylate), poly(ethyl acrylate), poly(n-propyl acrylate), poly(isopropyl acrylate), poly(n-butyl acrylate), poly(t-butyl acrylate), poly(sec-butyl acrylate), poly(pentyl acrylate), poly(2-ethylhexyl acrylate), poly(2-ethylbutyl acrylate), poly(n-octyl acrylate), poly(isobornyl acrylate), poly(isooctyl acrylate), poly(isononyl acrylate), poly(lauryl acrylate) and blends or copolymers thereof.

18. The imbibed substrate of claim 12, further comprising one or more of methyl salicylate, ethyl salicylate, arnica oil, peppermint oil, menthol, lidocaine, benzocaine, capsaicin, nonivamide, niacinamide, cannabidiol, caffeine, and hydrocortisone.

19. The imbibed substrate of claim 12, further comprising, in combination, a yarn, a thread, a filament, or a fiber without the polymer matrix imbibed thereon.

20. A textile comprising the imbibed substrate of claim 19.

* * * * *

UNITED STATES PATENT AND TRADEMARK OFFICE
CERTIFICATE OF CORRECTION

PATENT NO. : 10,799,464 B2  
APPLICATION NO. : 16/216581  
DATED : October 13, 2020  
INVENTOR(S) : David Anderson et al.

Page 1 of 1

It is certified that error appears in the above-identified patent and that said Letters Patent is hereby corrected as shown below:

In the Claims

In Column 50, Claim 18, please change Lines 51 and 52 to:
"nonivamide, niacinamide, caffeine, and hydrocortisone."

Signed and Sealed this
Twenty-ninth Day of December, 2020

Andrei Iancu
*Director of the United States Patent and Trademark Office*